United States Patent
Choi et al.

(10) Patent No.: US 9,614,163 B2
(45) Date of Patent: Apr. 4, 2017

(54) LIGHT-EMITTING DIODE HAVING NOVEL STRUCTURE AND ELECTRONIC APPARATUS COMPRISING SAME

(71) Applicant: LMS Co., Ltd., Pyeongtaek-si (KR)

(72) Inventors: Jeong Og Choi, Seoul (KR); Joon Ho Jung, Hwaseong-si (KR); Oh Kwan Kwon, Anyang-si (KR)

(73) Assignee: LMS Co., Ltd., Pyeongtaek-si (KR)

( * ) Notice: Subject to any disclaimer, the term of this patent is extended or adjusted under 35 U.S.C. 154(b) by 74 days.

(21) Appl. No.: 14/429,948

(22) PCT Filed: Sep. 18, 2013

(86) PCT No.: PCT/KR2013/008466
§ 371 (c)(1),
(2) Date: Jul. 27, 2015

(87) PCT Pub. No.: WO2014/046495
PCT Pub. Date: Mar. 27, 2014

(65) Prior Publication Data
US 2016/0043326 A1   Feb. 11, 2016

(30) Foreign Application Priority Data

Sep. 21, 2012 (KR) .................. 10-2012-0105153
Aug. 29, 2013 (KR) .................. 10-2013-0103512

(51) Int. Cl.
*H01L 51/50* (2006.01)
*H01L 51/00* (2006.01)
(Continued)

(52) U.S. Cl.
CPC ........ *H01L 51/0072* (2013.01); *C07D 405/14* (2013.01); *C07D 409/14* (2013.01);
(Continued)

(58) Field of Classification Search
None
See application file for complete search history.

(56) References Cited

U.S. PATENT DOCUMENTS 8,309,947 B2   11/2012  Vaufrey
8,592,055 B2   11/2013  Balaganesan et al.
(Continued)

FOREIGN PATENT DOCUMENTS

KR   1020110104452 A   9/2011
KR   1020110137712 A   12/2011
(Continued)

*Primary Examiner* — Gregory Clark
(74) *Attorney, Agent, or Firm* — The Webb Law Firm

(57) ABSTRACT

A light-emitting diode includes: a first electrode; a second electrode; a light-emitting layer disposed between the first electrode and the second electrode; a hole transportable layer disposed between the first electrode and the light-emitting layer; and a blocking layer, which is disposed between the hole transportable layer and the light-emitting layer and includes a compound represented by the following Chemical Formula 1.

[Chemical Formula 1]

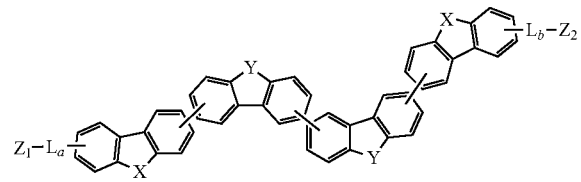

16 Claims, 3 Drawing Sheets

(51) Int. Cl.
*C09K 11/06* (2006.01)
*C09K 11/02* (2006.01)
*C07D 405/14* (2006.01)
*C07D 409/14* (2006.01)
*C07F 7/08* (2006.01)

(52) U.S. Cl.
CPC .......... *C07F 7/0816* (2013.01); *C09K 11/025* (2013.01); *C09K 11/06* (2013.01); *H01L 51/0052* (2013.01); *H01L 51/0058* (2013.01); *H01L 51/0061* (2013.01); *H01L 51/0073* (2013.01); *H01L 51/0074* (2013.01); *H01L 51/0094* (2013.01); *H01L 51/006* (2013.01); *H01L 51/506* (2013.01); *H01L 51/5056* (2013.01); *H01L 51/5064* (2013.01); *H01L 51/5096* (2013.01)

(56) References Cited

U.S. PATENT DOCUMENTS

| 2011/0018429 | A1* | 1/2011 | Spindler | C09K 11/06 313/504 |
|---|---|---|---|---|
| 2012/0168731 | A1 | 7/2012 | Schildknecht et al. | |
| 2012/0232241 | A1 | 9/2012 | Stoessel et al. | |
| 2012/0273767 | A1* | 11/2012 | Yokoyama | H01L 51/0072 257/40 |

FOREIGN PATENT DOCUMENTS

| KR | 1020120052936 A | 5/2012 | |
|---|---|---|---|
| KR | 1020120095997 A | 8/2012 | |
| WO | WO 2012/115034 | * 8/2012 | ............. H01L 51/50 |

\* cited by examiner

LIGHT-EMITTING DIODE HAVING NOVEL STRUCTURE AND ELECTRONIC APPARATUS COMPRISING SAME

CROSS-REFERENCE TO RELATED APPLICATIONS

This application is the United States national phase of International Application No. PCT/KR2013/008466 filed Sep. 18, 2013, and claims priority to Korean Patent Application Nos. 10-2012-0105153 and 10-2013-0103512 filed Sep. 21, 2012 and Aug. 29, 2013, respectively, the disclosures of which are hereby incorporated in their entirety by reference.

BACKGROUND

Field of the Invention

The present invention relates to a light-emitting diode having a novel structure and an electronic apparatus including the same.

Background Art

In general, a light-emitting diode includes two electrodes facing each other and a light-emitting layer including a light-emitting compound interposed between the electrodes. When current flows between the electrodes, the light-emitting compound produces light. A display device using the light-emitting diode does not need a separate light source device, and thus may decrease the weight, size or thickness of the display device. Further, the display device using the light-emitting diode has an advantage in that the viewing angle, the contrast ratio, the color reproducibility, and the like are excellent and power consumption is low as compared to a display device using a backlight and a liquid crystal.

The materials used as an organic material layer of an organic light-emitting diode among the light-emitting diodes may be classified into a light-emitting material, a hole injection material, a hole transport material, an electron transport material, an electron injection material, and the like according to the function. The light-emitting materials may be divided into a polymer-type and a low molecular weight-type according to the molecular weight, and may be divided into blue, green, red light-emitting materials, and the like according to the light-emitting color.

When a single material is used as a light-emitting material, there may occur a problem in that the maximum light-emitting wavelength is moved into the long wavelength by the interaction between molecules, the color purity is reduced, or efficiency of the diode is lowered by the light-emitting reducing effect. In order to complement the problem, a light-emitting layer composed of a host/dopant system may be applied to the light-emitting diode. An exciton formed in the light-emitting layer is transferred to a dopant by using a host material, which is a main material forming the light-emitting layer, and a small amount of the dopant having an energy band gap lower than that of the host, so that the light-emitting diode may efficiently emit light.

However, the light-emitting diode still has a problem in that light emission has a lifespan and the power efficiency is low. In order to solve these problems, various compounds have been developed as a material for the light-emitting diode, but there is a limitation in manufacturing a light-emitting diode which satisfies both the light emission lifespan and the power efficiency.

SUMMARY OF THE INVENTION

Technical Problem

Thus, a technical problem of the present invention has been contrived in view of these circumstances, and an object of the present invention is to provide a novel structure which may enhance the light emission efficiency and increase the lifespan in a light-emitting diode.

Another object of the present invention is to provide an electronic apparatus including the light-emitting diode.

Technical Solution

A light-emitting diode according to an exemplary embodiment for implementing the object of the present invention includes: a first electrode; a second electrode; a light-emitting layer disposed between the first electrode and the second electrode; a hole transportable layer disposed between the first electrode and the light-emitting layer; and a blocking layer, which is disposed between the hole transportable layer and the light-emitting layer and includes a compound represented by the following Chemical Formula 1.

[Chemical Formula 1]

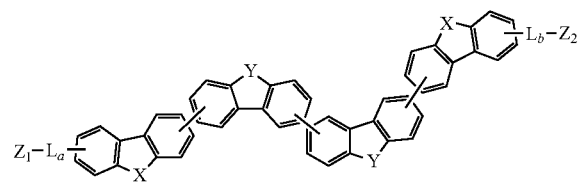

In the Chemical Formula,

X and Y each independently represent $N-L_c-Ar_1$, S, O, or $Si(R_1)(R_2)$, one of X and Y is $N-L_c-Ar_1$, and the other is S, O, or $Si(R_1)(R_2)$, $Z_1$ and $Z_2$ each independently represent hydrogen, an alkyl group having 1 to 6 carbon atoms, an aryl group having 6 to 30 carbon atoms, a heteroaryl group having 2 to 20 carbon atoms, or the following Chemical Formula 2 or the following Chemical Formula 3,

[Chemical Formula 2]

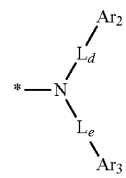

[Chemical Formula 3]

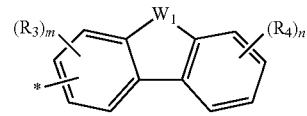

$Ar_1$, $Ar_2$ and $Ar_3$ each independently represent hydrogen, an alkyl group having 1 to 6 carbon atoms, an aryl group having 6 to 30 carbon atoms, a heteroaryl group having 2 to 20 carbon atoms, a cycloalkyl group having 3 to 20 carbon atoms, a heterocycloalkyl group having 2 to 20 carbon atoms, a bicycloalkyl group having 7 to 20 carbon atoms, or the following Chemical Formula 4,

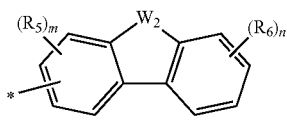

[Chemical Formula 4]

$W_1$ and $W_2$ each independently represent $N$-$L_f$-$Ar_4$, O, S, or $Si(R_7)(R_8)$, $R_1$, $R_2$, $R_7$, and $R_8$ each independently represent an alkyl group having 1 to 6 carbon atoms, an aryl group having 6 to 30 carbon atoms, or a heteroaryl group having 2 to 20 carbon atoms, $R_3$, $R_4$, $R_5$, and $R_6$ each independently represent hydrogen, an alkyl group having 1 to 6 carbon atoms, an aryl group having 6 to 30 carbon atoms, or a heteroaryl group having 2 to 20 carbon atoms, independently in each of Chemical Formulae 3 and 4, m represents an integer of 0 to 3 and n represents an integer of 0 to 4, $L_a$, $L_b$, $L_c$, $L_d$, $L_e$, and $L_f$ each independently represent *-$L_1$-$L_2$-$L_3$-$L_4$-*, $L_1$, $L_2$, $L_3$, and $L_4$ each independently represent a single bond, —O—, —S—, a linear or branched alkylene group (—$(CH_2)_j$—, here, j is an integer of 1 to 20) having 1 to 20 carbon atoms, an arylene group having 6 to 20 carbon atoms, a heteroarylene group having 2 to 20 carbon atoms, a cycloalkylene group having 3 to 20 carbon atoms, a heterocycloalkylene group 2 to 20 carbon atoms, or a bicycloalkylene group having 7 to 20 carbon atoms, $Ar_4$ represents hydrogen, an alkyl group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, or a bicycloalkyl group having 7 to 30 carbon atoms, and one or more of the hydrogens of Chemical Formula 1 are each independently unsubstituted or substituted with one or more substituents selected from the group consisting of an alkyl group having 1 to 6 carbon atoms, an alkoxy group having 1 to 6 carbon atoms, an amine group substituted with one or more alkyl groups having 1 to 6 carbon atoms, an aryl group having 6 to 30 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

Further, the present invention discloses an electronic apparatus including the light-emitting diode.

Effect of the Invention

The light-emitting diode according to the present invention provides enhanced light-emitting efficiency, an increased lifespan, and excellent thermal stability (heat resistance).

DETAILED DESCRIPTION OF THE INVENTION

Figure 1:
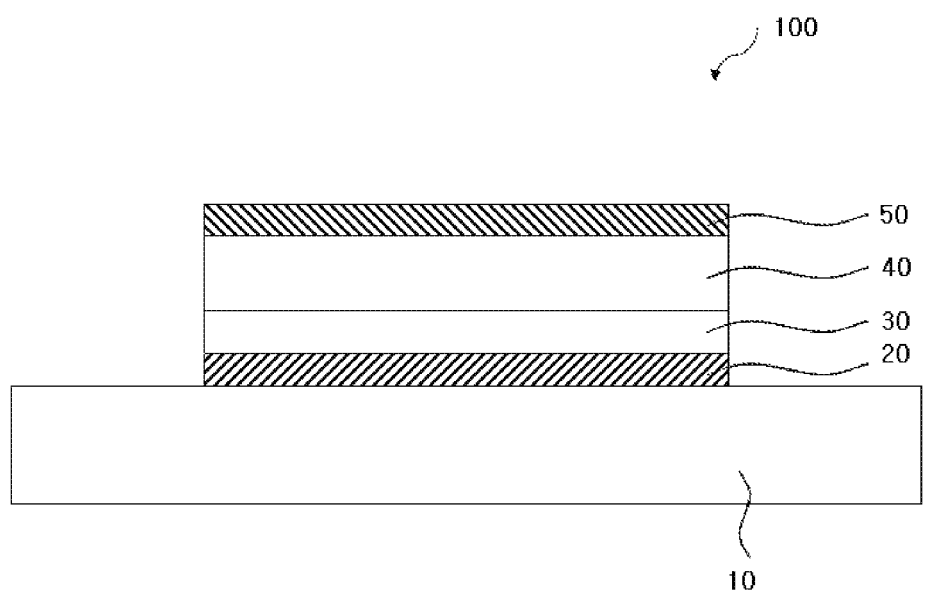
FIG. 1 is a cross-sectional view for describing a light-emitting diode according to an exemplary embodiment of the present invention.

A light-emitting diode according to the present invention includes a first electrode, a second electrode, a light-emitting layer disposed between the first electrode and the second electrode, a hole transportable layer disposed between the first electrode and the light-emitting layer, and a blocking layer, which is disposed between the hole transportable layer and the light-emitting layer and includes a compound represented by the following Chemical Formula 1.

[Chemical Formula 1]

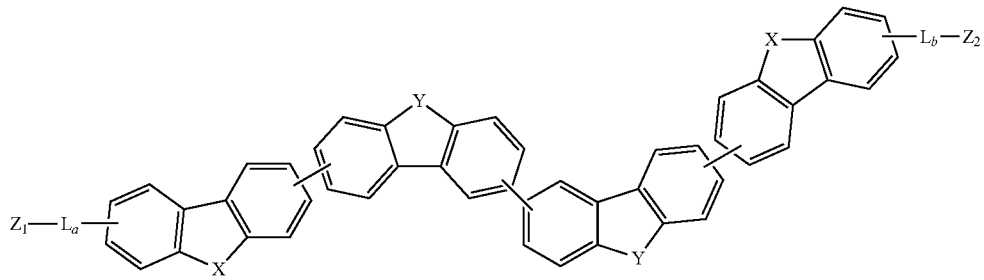

In the Chemical Formula,

X and Y each independently represent $N$-$L_c$-$Ar_1$, S, O, or $Si(R_1)(R_2)$, one of X and Y is $N$-$L_c$-$Ar_1$, and the other is S, O, or $Si(R_1)(R_2)$, $Z_1$ and $Z_2$ each independently represent hydrogen, an alkyl group having 1 to 6 carbon atoms, an aryl group having 6 to 30 carbon atoms, a heteroaryl group having 2 to 20 carbon atoms, and the following Chemical Formula 2 or the following Chemical Formula 3,

[Chemical Formula 2]

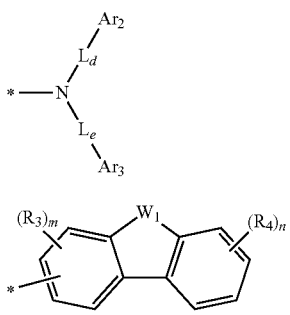

[Chemical Formula 3]

Ar$_1$, Ar$_2$, and Ar$_3$ each independently represent hydrogen, an alkyl group having 1 to 6 carbon atoms, an aryl group having 6 to 30 carbon atoms, a heteroaryl group having 2 to 20 carbon atoms, a cycloalkyl group having 3 to 20 carbon atoms, a heterocycloalkyl group having 2 to 20 carbon atoms, a bicycloalkyl group having 7 to 20 carbon atoms, or the following Chemical Formula 4,

[Chemical Formula 4]

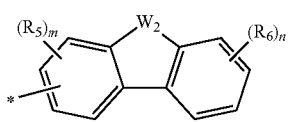

W$_1$ and W$_2$ each independently represent N-L$_f$-Ar$_4$, O, S, or Si(R$_7$)(R$_8$), R$_1$, R$_2$, R$_7$, and R$_8$ each independently represent an alkyl group having 1 to 6 carbon atoms, an aryl group having 6 to 30 carbon atoms, or a heteroaryl group having 2 to 20 carbon atoms, R$_3$, R$_4$, R$_5$, and R$_6$ each independently represent hydrogen, an alkyl group having 1 to 6 carbon atoms, an aryl group having 6 to 30 carbon atoms, or a heteroaryl group having 2 to 20 carbon atoms, independently in each of Chemical Formulae 3 and 4, m represents an integer of 0 to 3 and n represents an integer of 0 to 4, L$_a$, L$_b$, L$_c$, L$_d$, L$_e$, and L$_f$ each independently represent *-L$_1$-L$_2$-L$_3$-L$_4$-*, L$_1$, L$_2$, L$_3$, and L$_4$ each independently represent a single bond, —O—, —S—, a linear or branched alkylene group (—(CH$_2$)$_j$—, here, j is an integer of 1 to 20) having 1 to 20 carbon atoms, an arylene group having 6 to 20 carbon atoms, a heteroarylene group having 2 to 20 carbon atoms, a cycloalkylene group having 3 to 20 carbon atoms, a heterocycloalkylene group 2 to 20 carbon atoms, or a bicycloalkylene group having 7 to 20 carbon atoms, Ar$_4$ represents hydrogen, an alkyl group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, or a bicycloalkyl group having 7 to 30 carbon atoms, and one or more of the hydrogens of Chemical Formula 1 are each independently unsubstituted or substituted with one or more substituents selected from the group consisting of an alkyl group having 1 to 6 carbon atoms, an alkoxy group having 1 to 6 carbon atoms, an amine group substituted with one or more alkyl groups having 1 to 6 carbon atoms, an aryl group having 6 to 30 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group. In the present invention, "an alkyl group" is defined as a functional group derived from a linear or branched, saturated hydrocarbon.

Specific examples of the alkyl group include a methyl group, an ethyl group, an n-propyl group, an iso-propyl group, an n-butyl group, a sec-butyl group, a tert-butyl group, an n-pentyl group, a 1,1-dimethylpropyl group, a 1,2-dimethylpropyl group, a 2,2-dimethylpropyl group, a 1-ethylpropyl group, a 2-ethylpropyl group, an n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group, and the like.

The alkyl group has 1 to 20 carbon atoms, for example, 1 to 12 carbon atoms, 1 to 6 carbon atoms, or 1 to 4 carbon atoms.

In the present invention, "an aryl group" is defined as a monovalent substituent derived from an aromatic hydrocarbon.

Specific examples of the aryl group include a phenyl group, a naphthyl group, an anthracenyl group, a naphthacenyl group, a pyrenyl group, a tolyl group, a biphenyl group, a terphenyl group, a chrycenyl group, a spirobifluorenyl group, a fluoranthenyl group, a fluorenyl group, a perylenyl group, an indenyl group, an azulenyl group, a heptalenyl group, a phenalenyl group, a phenanthrenyl group, and the like.

The aryl group has 6 to 30 carbon atoms, for example, 6 to 18 carbon atoms, or 6 to 12 carbon atoms.

"A heteroaryl group" represents "an aromatic heterocyclic ring" derived from a monocyclic or fused ring. The heteroaryl group may include at least one, for example, one, two, three or four of nitrogen (N), sulfur (S), oxygen (O), phosphorus (P), selenium (Se), and silicon (Si) as a heteroatom.

Specific examples of the heteroaryl group include a nitrogen-containing heteroaryl group including a pyrrolyl group, a pyridyl group, a pyridazinyl group, a pyrimidinyl group, a pyrazinyl group, a triazolyl group, a tetrazolyl group, a benzotriazolyl group, a pyrazolyl group, an imidazolyl group, a benzimidazolyl group, an indolyl group, an isoindolyl group, an indolizinyl group, a purinyl group, an indazolyl group, a quinolyl group, an isoquinolinyl group, a quinolizinyl group, a phthalazinyl group, a naphthylidinyl group, a quinoxalinyl group, a quinazolinyl group, a cinnolinyl group, a pteridinyl group, an imidazotriazinyl group, an acridinyl group, a phenanthridinyl group, a carbazolyl group, a phenanthrolinyl group, a phenazinyl group, an imidazopyridinyl group, an imidazopyrimidinyl group, a pyrazolopyridinyl group, and the like; a sulfur-containing heteroaryl group including a thienyl group, a benzothienyl group, a dibenzothienyl group, and the like; an oxygen-containing heteroaryl group including a furyl group, a pyranyl group, a cyclopentapyranyl group, a benzofuranyl group, an isobenzofuranyl group, a dibenzofuranyl group, and the like; and the like. In addition, specific examples of the heteroaryl group compounds including at least two heteroatoms, such as a thiazolyl group, an isothiazolyl group, a benzothiazolyl group, a benzothiadiazolyl group, a phenothiazinyl group, an isoxazolyl group, a furazanyl group, a phenoxazinyl group, an oxazolyl group, a benzoxazolyl group, an oxadiazolyl group, a pyrazoloxazolyl group, an imidazothiazolyl group, a thienofuranyl group.

The heteroaryl group may have 2 to 20 carbon atoms, for example, 3 to 19 carbon atoms, 4 to 15 carbon atoms, or 5 to 11 carbon atoms. For example, when including a heteroatom, the heteroaryl group may have 5 to 21 ring members.

"A cycloalkyl group" is defined as a functional group derived from a monocyclic saturated hydrocarbon.

Specific examples of the cycloalkyl group include a cyclopropyl group, a cyclobutyl group, a cyclopentyl group, a cyclohexyl group, a cycloheptyl group or a cyclooctyl group, and the like.

The cycloalkyl group has 3 to 20 carbon atoms, for example, 3 to 12 carbon atoms, or 3 to 6 carbon atoms.

"A heterocycloalkyl group" is defined as a non-aromatic monocyclic or polycyclic group containing one or more heteroatoms in addition to a carbon atom as an element of the ring. The heteroatom may include an atom of oxygen (O), nitrogen (N), sulfur (S), selenium (Se), or phosphorus (P), and is not limited thereto. Furthermore, even though the heterocycloalkyl group does not include an aromatic ring, a bond, which links a carbon atom-a carbon atom or a carbon atom-a heteroatom constituting the ring of the heterocycloalkyl group, may include a double bond.

Specific examples of the heterocycloalkyl group include a 2-pyrrolidinyl group, a 3-pyrrolidinyl group, a piperidinyl group, a 2-tetrahydrofuranyl group, a 3-tetrahydrofuranyl group, a 2-tetrahydrothienyl group and a 3-tetrahydrothienyl group, but are not limited thereto.

The heterocycloalkyl group has 2 to 20 carbon atoms, for example, 3 to 19 carbon atoms, or 5 to 11 carbon atoms. That is, when including a heteroatom, the heterocycloalkyl group has 3 to 21 ring members, for example, 4 to 20 ring members, or 6 to 12 ring members.

"A bicycloalkyl group" means a functional group in which at least one carbon atom selected from each of the two alkyl rings is linked to each other.

Specific examples of the bicycloalkyl group include a bicyclopentyl group, a bicyclohexyl group, a bicycloheptyl group, a bicyclootyl group, a bicyclononyl group or a bicyclodecyl group, and the like.

The bicycloalkyl group has 5 to 20 carbon atoms, for example, 7 to 18 carbon atoms, or 7 to 12 carbon atoms.

Further, "an arylene group" may mean a divalent substituent derived from the aryl group described above.

In addition, "a heteroarylene group" may mean a divalent substituent derived from the heteroaryl group described above.

In a heteroaryl having three rings in the present invention, the position of a carbon atom which may substitute or be substituted is denoted as follows based on the heteroatom, and will be described below based on this.

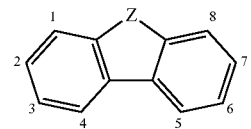

A light-emitting diode according to the present invention includes a blocking layer disposed between a hole transportable layer and a light-emitting layer. The blocking layer may be an electron blocking layer (EBL) which prevents electrons injected from a second electrode from flowing into the hole transportable layer via the light-emitting layer. Further, the blocking layer may be an exciton blocking layer which prevents an exciton formed in the light-emitting layer from being diffused in a direction of a first electrode, and thus being non-radiatively decayed.

In addition, the blocking layer may be an exciton dissociation blocking layer (EDBL). The exciton dissociation blocking layer may prevent an exciton formed in a light-emitting layer from being non-radiatively decayed through the process of exciton dissociation at the interface between the light-emitting layer and the hole transportable layer. In order to prevent exciton dissociation at the interface, a compound which forms the blocking layer may be selected so as to have a HOMO value at a level similar to that of a compound which forms the light-emitting layer.

When the thickness of the blocking layer is adjusted so as to be suitable for the resonant length of the light-emitting diode, the light-emitting efficiency may be increased, and the thickness may be adjusted such that an exciton may be formed at the central portion of the light-emitting layer other than the interface between the light-emitting layer and another layer.

In an exemplary embodiment, the compound of Chemical Formula 1 may be represented by the following Chemical Formula 5.

[Chemical Formula 5]

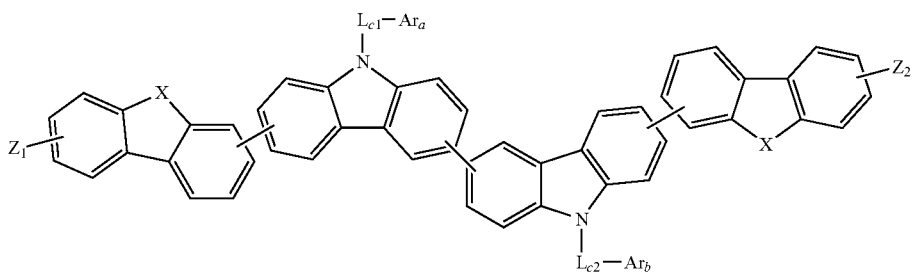

In the Chemical Formula,

X represents S, O, or $Si(R_1)(R_2)$, $L_{c1}$ and $L_{c2}$ each independently represent a single bond, —O—, —S—, an arylene group having 6 to 20 carbon atoms, a heteroarylene group having 2 to 20 carbon atoms, or a cycloalkylene group having 3 to 20 carbon atoms, $Z_1$ and $Z_2$ each independently represent hydrogen, an alkyl group having 1 to 6 carbon atoms, an aryl group having 6 to 30 carbon atoms, a heteroaryl group having 2 to 20 carbon atoms, or the following Chemical Formula 6 or the following Chemical Formula 7,

[Chemical Formula 6]
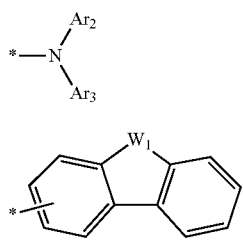

[Chemical Formula 7]
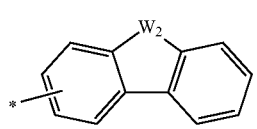

$Ar_a$, $Ar_b$, $Ar_2$, and $Ar_3$ each independently represent hydrogen, an alkyl group having 1 to 12 carbon atoms, an aryl group having 6 to 30 carbon atoms, or the following Chemical Formula 8,

[Chemical Formula 8]
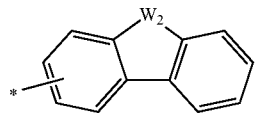

$W_1$ and $W_2$ each independently represent N—$Ar_4$, O, S, or $Si(R_7)(R_8)$, $R_1$, $R_2$, $R_7$, and $R_8$ each independently represent an alkyl group having 1 to 6 carbon atoms, or an aryl group having 6 to 30 carbon atoms, $Ar_4$ represents an alkyl group having 1 to 12 carbon atoms, or an aryl group having 6 to 30 carbon atoms, and one or more of the hydrogens of $Ar_a$, $Ar_b$, $Ar_2$, $Ar_3$, and $Ar_4$ are each independently unsubstituted or substituted with one or more substituents selected from the group consisting of an alkyl group having 1 to 6 carbon atoms, an alkoxy group having 1 to 6 carbon atoms, an amine group substituted with one or more alkyl groups having 1 to 6 carbon atoms, and an aryl group having 6 to 30 carbon atoms.

In another exemplary embodiment, the compound represented by Chemical Formula 5 may be represented by the following Chemical Formula 9.

[Chemical Formula 9]
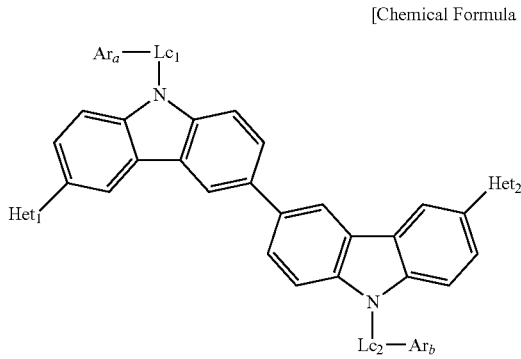

In the Chemical Formula, $L_{c1}$ and $L_{c2}$ each independently represent a single bond, —O—, —S—, an arylene group having 6 to 20 carbon atoms, a heteroarylene group having 2 to 20 carbon atoms, or a cycloalkylene group having 3 to 20 carbon atoms, $Ar_a$ and $Ar_b$ each independently represent hydrogen, an alkyl group having 1 to 12 carbon atoms, an aryl group having 6 to 30 carbon atoms, or the following Chemical Formula 8,

[Chemical Formula 8]
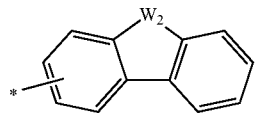

$Het_1$ and $Het_2$ represent the following Chemical Formula 10 or the following Chemical Formula 11,

[Chemical Formula 10]
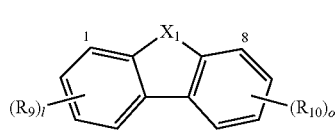

[Chemical Formula 11]
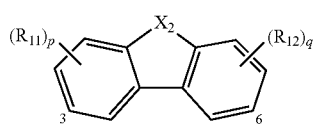

here, $W_2$ represents N—$Ar_4$, O, S, or $Si(R_7)(R_8)$, $Ar_4$ represents hydrogen, an alkyl group having 1 to 12 carbon atoms, or an aryl group having 6 to 30 carbon atoms, $X_1$ represents S or O, $X_2$ represents S, $R_7$, $R_8$, $R_9$, $R_{10}$, $R_{11}$, and $R_{12}$ each independently represent an alkyl group having 1 to 6 carbon atoms, an aryl group having 6 to 30 carbon atoms, or a heteroaryl group having 2 to 20 carbon atoms, l, o, p, and q each independently represent an integer of 0 to 3, the substituent represented by Chemical Formula 10 is substituted with the compound of Chemical Formula 1 at the position of the 1st or 8th carbon, and the substituent represented by Chemical Formula 11 is substituted with the compound of Chemical Formula 1 at the position of the 3rd or 6th carbon.

For example, in Chemical Formula 9, whether $Het_1$ and $Het_2$ is the substituent represented by Chemical Formula 10 or the substituent represented by Chemical Formula 11 may affect physical properties of the compound. The inventors of the present invention have confirmed through repeated and various experiments that in the case where $Het_1$ and $Het_2$ in Chemical Formula 9 are the substituent represented by Chemical Formula 10, when $Het_1$ and $Het_2$ are applied to a light-emitting diode, the service life of the diode may be enhanced without reducing the power efficiency.

In still another exemplary embodiment, in Chemical Formula 5,

X represents S, O, or $Si(R_1)(R_2)$, $R_1$ and $R_2$ each represent a methyl group or a phenyl group, $Z_1$ and $Z_2$ each independently represent hydrogen, a carbazolyl group, a dibenzofuranyl group, a dibenzothiophenyl group, a dibenzosilolyl group, or a diphenylamine group, and here, the carbazolyl group, the dibenzofuranyl group, the dibenzothiophenyl group, or the dibenzosilolyl group is each independently unsubstituted or substituted with one or more substituents selected from the group consisting of an alkyl group having 1 to 6 carbon atoms and an aryl group having 6 to 30 carbon atoms, and $Ar_a$ and $Ar_b$ may each independently represent a phenyl group, a biphenyl group, a naphthyl group, a dibenzofuranyl group, or a dibenzothiophenyl group.

In yet another exemplary embodiment, the compound of Chemical Formula 1 may be represented by the following Chemical Formula 12.

[Chemical Formula 12]

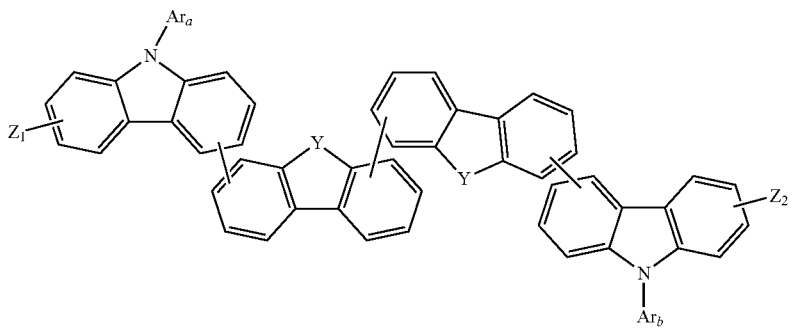

In the Chemical Formula,

Y represents S, O, or $Si(R_1)(R_2)$, $Z_1$ and $Z_2$ each independently represent hydrogen, the following Chemical Formula 13, or the following Chemical Formula 14,

[Chemical Formula 13]

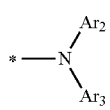

[Chemical Formula 14]

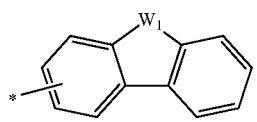

$Ar_a$, $Ar_b$, $Ar_2$, and $Ar_3$ each independently represent hydrogen, an alkyl group having 1 to 12 carbon atoms, an aryl group having 6 to 30 carbon atoms, or the following Chemical Formula 15,

[Chemical Formula 15]

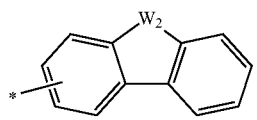

$W_1$ and $W_2$ each independently represent N—$Ar_4$, O, S, or $Si(R_7)(R_8)$, $R_1$, $R_2$, $R_7$, and $R_8$ each independently represent an alkyl group having 1 to 6 carbon atoms, or an aryl group having 6 to 30 carbon atoms, $Ar_4$ represents an alkyl group having 1 to 12 carbon atoms, or an aryl group having 6 to 30 carbon atoms, and one or more of the hydrogens of $Ar_a$, $Ar_b$, $Ar_2$, $Ar_3$, and $Ar_4$ are each independently unsubstituted or substituted with one or more substituents selected from the group consisting of an alkyl group having 1 to 6 carbon atoms, an alkoxy group having 1 to 6 carbon atoms, and an amine group substituted with one or more alkyl groups having 1 to 6 carbon atoms.

In still yet another exemplary embodiment, the compound represented by Chemical Formula 12 may be represented by the following Chemical Formula 16.

[Chemical Formula 16]

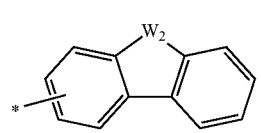

In the Chemical Formula,

Y represents S, O, or $Si(R_1)(R_2)$, $Ar_a$ and $Ar_b$ each independently represent an alkyl group having 1 to 6 carbon atoms, an aryl group having 6 to 30 carbon atoms, or the following Chemical Formula 17,

[Chemical Formula 17]

$W_2$ represents N—$Ar_4$, O, S, or $Si(R_7)(R_8)$, $R_1$, $R_2$, $R_7$, and $R_8$ each independently represent an alkyl group having 1 to 6 carbon atoms, or an aryl group having 6 to 30 carbon atoms, and $Ar_4$ represents an alkyl group having 1 to 6 carbon atoms, or an aryl group having 6 to 30 carbon atoms.

In a further exemplary embodiment, in Chemical Formula 12,

Y represents S, O, or $Si(R_1)(R_2)$, $R_1$ and $R_2$ each represent a methyl group or a phenyl group, $Z_1$ and $Z_2$ each independently represent hydrogen, a carbazolyl group, a dibenzofuranyl group, a dibenzothiophenyl group, a dibenzosilolyl group, or a diphenylamine group, and here, the carbazolyl group, the dibenzofuranyl group, the dibenzothiophenyl group, or the dibenzosilolyl group is each independently unsubstituted or substituted with one or more substituents selected from the group consisting of an alkyl group having 1 to 6 carbon atoms and an aryl group having 6 to 30 carbon atoms, and Ar$_a$ and Ar$_b$ may each independently represent a phenyl group, a biphenyl group, a naphthyl group, a dibenzofuranyl group, or a dibenzothiophenyl group.

In an exemplary embodiment, a hole transportable layer may include a compound represented by the following Chemical Formula 18.

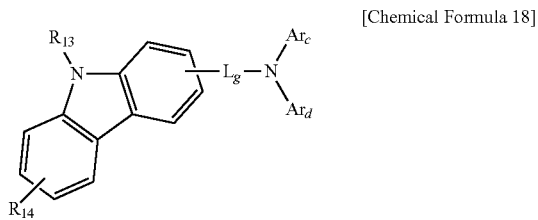

[Chemical Formula 18]

In the Chemical Formula,

R$_{13}$ and R$_{14}$ each independently represent hydrogen, an alkyl group having 1 to 6 carbon atoms, an aryl group having 6 to 30 carbon atoms, or a heteroaryl group having 2 to 20 carbon atoms, L$_g$ each independently represents *-L$_5$-L$_6$-L$_7$-L$_8$-*, L$_5$, L$_6$, L$_7$, and L$_8$ each independently represent a single bond, —O—, —S—, an arylene group having 6 to 20 carbon atoms, a heteroarylene group having 2 to 20 carbon atoms, or a cycloalkylene group having 3 to 20 carbon atoms, and the case where L$_5$, L$_6$, L$_7$, and L$_8$ are all a single bond is excluded, Ar$_c$ and Ar$_d$ each independently represent an aryl group having 6 to 30 carbon atoms, a heteroaryl group having 2 to 20 carbon atoms, or the following Chemical Formula 19,

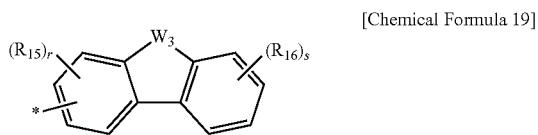

[Chemical Formula 19]

W$_3$ represents O, S, or C(R$_{17}$)(R$_{18}$),

R$_{15}$, R$_{16}$, R$_{17}$, and R$_{18}$ each independently represent an alkyl group having 1 to 6 carbon atoms, an aryl group having 6 to 30 carbon atoms, or a heteroaryl group having 2 to 20 carbon atoms, r represents an integer of 0 to 3, and s represents an integer of 0 to 4.

In another further exemplary embodiment, the compound represented by Chemical Formula 18 may be represented by the following Chemical Formula 20.

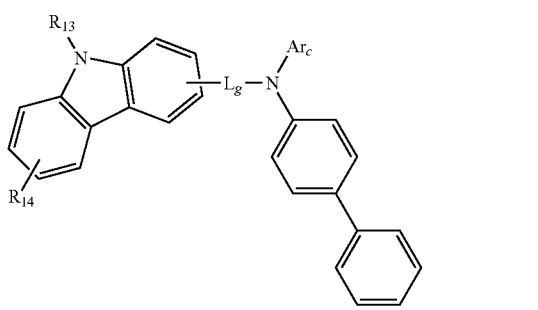

[Chemical Formula 20]

In the Chemical Formula,

R$_{13}$ represents an aryl group having 6 to 30 carbon atoms,

R$_{14}$ represents hydrogen,

L$_g$ represents an arylene group having 6 to 20 carbon atoms,

Ar$_c$ represents an aryl group having 6 to 30 carbon atoms, or the following Chemical Formula 21,

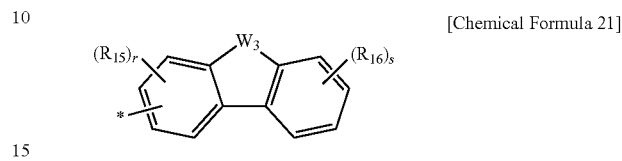

[Chemical Formula 21]

W$_3$ represents O, S, or C(R$_{17}$)(R$_{18}$),

R$_{15}$, R$_{16}$, R$_{17}$, and R$_{18}$ each independently represent an alkyl group having 1 to 6 carbon atoms, or an aryl group having 6 to 30 carbon atoms, r represents an integer of 0 to 2, and s represents an integer of 0 to 2.

As an example, in Chemical Formula 20,

R$_{13}$ represents a phenyl group, a biphenyl group, a terphenyl group, or a naphthyl group, R$_{14}$ represents hydrogen, L$_g$ represents a phenylene group, a biphenylene group, a terphenylene group, or a naphthylene group, and Ar$_c$ may represent a phenyl group, a biphenyl group, a terphenyl group, a naphthyl group, dibenzothiophenyl group, a dibenzofuranyl group, a fluorenyl group, a dimethylfluorenyl group, or a diphenylfluorenyl group.

Further, the hole transportable layer may include: a first layer which may include a P-type dopant; and a second layer including the compound of Chemical Formula 18.

The light-emitting layer may include a compound represented by the following Chemical Formula 22.

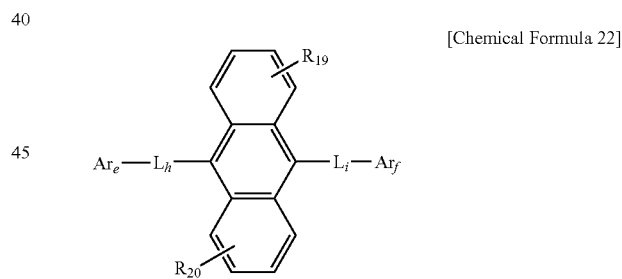

[Chemical Formula 22]

In the Chemical Formula,

R$_{19}$ and R$_{20}$ each independently represent hydrogen, an alkyl group having 1 to 6 carbon atoms, an aryl group having 6 to 30 carbon atoms, or a heteroaryl group having 2 to 20 carbon atoms, L$_h$ and L$_i$ each independently represent *-L$_9$-L$_{10}$-*, L$_9$ and L$_{10}$ each independently represent a single bond, an arylene group having 6 to 20 carbon atoms, or a heteroarylene group having 2 to 20 carbon atoms, and Ar$_e$ and Ar$_f$ each independently represent an aryl group having 6 to 30 carbon atoms, or a heteroaryl group having 2 to 20 carbon atoms.

As an example, in Chemical Formula 22,

R$_{19}$ and R$_{20}$ each independently represent hydrogen, or an alkyl group having 1 to 6 carbon atoms, L$_h$ and L$_i$ each independently represent *-L$_9$-L$_{10}$-*, $L_9$ and $L_{10}$ each independently represent a single bond, a phenylene group, or a naphthylene group, and $Ar_e$ and $Ar_f$ may each independently represent an aryl group having 6 to 30 carbon atoms, or a heteroaryl group having 2 to 20 carbon atoms.

As an example, the light-emitting layer may additionally include a compound represented by the following Chemical Formula 23.

[Chemical Formula 23]

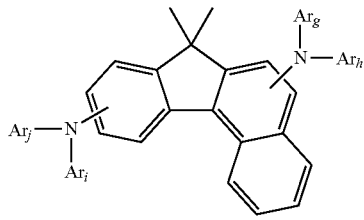

In the Chemical Formula, $Ar_g$, $Ar_h$, $Ar_i$, and $Ar_j$ each independently represent an alkyl group having 1 to 6 carbon atoms, an aryl group having 6 to 30 carbon atoms, which is unsubstituted or substituted with a trimethylsilyl group or a cyano group, or a heteroaryl group having 2 to 20 carbon atoms.

Furthermore, the present invention provides an electronic apparatus including the light-emitting diode previously described. Examples of the electronic apparatus are not particularly limited, and may be a display device, or a lighting device.

Hereinafter, a light-emitting diode according to the present invention will be described with reference to the accompanying drawings. Hereinafter, the structure of the light-emitting diode according to the present invention is not limited to the accompanying drawings and the following description.

FIG. 1 is a cross-sectional view for describing a light-emitting diode according to an exemplary embodiment of the present invention.

Referring to FIG. 1, a light-emitting diode 100 includes a first electrode 20, a hole transportable layer 30, a blocking layer 40, a light-emitting layer 50, and a second electrode 60, which are formed on a base substrate 10. The light-emitting diode 100 may be an organic light emitting diode (OLED).

The first electrode 20 may be formed of a conductive material on the base substrate 10. As an example, the first electrode 20 may be a transparent electrode. In this case, the first electrode 20 may be formed of indium tin oxide (ITO). In contrast, the first electrode 20 may be an opaque (reflective) electrode. In this case, the first electrode 20 may have an ITO/silver (Ag)/ITO structure. The first electrode 20 may become an anode of the light-emitting diode 100.

The hole transportable layer 30 is formed on the first electrode 20, and thus interposed between the first electrode 20 and the blocking layer 40. The hole transportable layer 30 may include a hole transport layer and/or a hole injecting layer. As an example, the hole transportable layer 30 may include a compound represented by the following Chemical Formula 18.

[Chemical Formula 18]

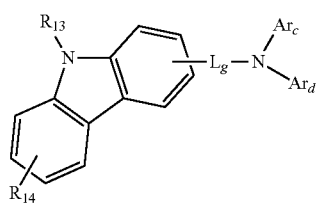

The compound represented by Chemical Formula 18 may be substantially the same as those previously described. Accordingly, the overlapping specific description of each of $R_{13}$, $R_{14}$, $L_g$, $Ar_c$, and $Ar_d$ will be omitted.

The blocking layer 40 is disposed between the hole transportable layer 30 and the light-emitting layer 50, and thus may serve a role of an electron blocking layer (EBL), an exciton blocking layer, or an exciton dissociation blocking layer (EDBL). For example, the blocking layer 40 may include a compound represented by Chemical Formula 1.

[Chemical Formula 1]

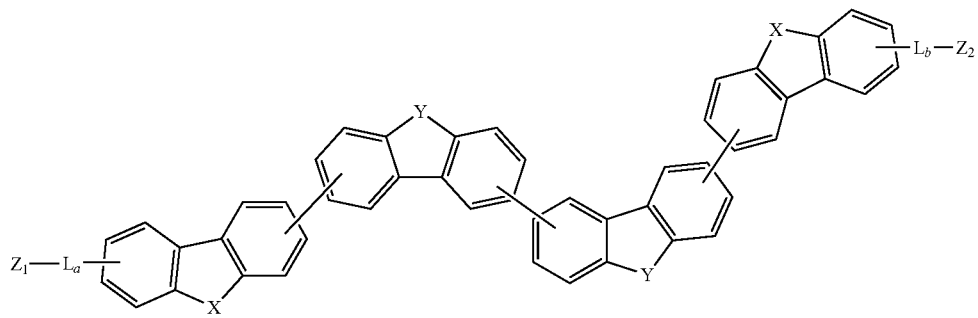

The compound represented by Chemical Formula 1 may be substantially the same as those previously described. Accordingly, the overlapping specific description of each of X, Y, $L_a$, $L_b$, $Z_1$, and $Z_2$ will be omitted.

The light-emitting layer 50 may be disposed between the blocking layer 40 and the second electrode 60. The wavelength of light emitted by the light-emitting layer 50 may vary depending on the kind of compound which forms the light-emitting layer 50. As a material which forms the light-emitting layer 50, various commercially available materials may be used without a particular limitation. For example, the light-emitting layer 50 may include a compound represented by the following Chemical Formula 22.

[Chemical Formula 22]

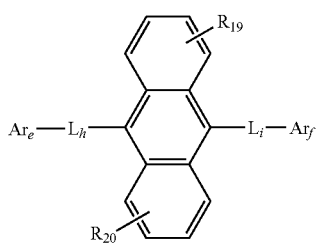

The compound represented by Chemical Formula 22 may be substantially the same as those previously described. Accordingly, the overlapping specific description of each of $R_{19}$, $R_{20}$, $L_h$, $L_i$, $Ar_e$, and $Ar_f$ will be omitted.

The second electrode 60 may be formed by a conductive material on the light-emitting layer 50. When the first electrode 20 is a transparent electrode, the second electrode 60 may be an opaque (reflective) electrode. In this case, the second electrode 60 may be an aluminum electrode. In contrast, when the first electrode 20 is an opaque electrode, the second electrode 60 may be a transparent or semi-transparent electrode, and in this case, the second electrode 60 may have a thickness of 100 Å to 150 Å. As a material which forms the opaque transparent, an alloy including magnesium and silver may be used. The second electrode 60 may become a cathode of the light-emitting diode 100.

Even though not illustrated in the drawing, an electron transporting layer (ETL) and/or an electron injecting layer (EIL) may be formed as an electron transport layer between the light-emitting layer 50 and the second electrode 60. For each of the electron transporting layer or the electron injecting layer, various commercially available materials may be used without a particular limitation.

When current flows between the first and second electrodes 20 and 60 of the light-emitting diode 100, a hole injected from the first electrode 20 to the light-emitting layer 50 and an electron injected from the second electrode 60 to the light-emitting layer 50 combine with each other form an exciton. While the exciton is transferred to a bottom state, light having a wavelength at a specific band is produced. In this case, the exciton may be a singlet exciton, and may also be a triplet exciton. Accordingly, the light-emitting diode 100 may provide light to the outside.

Meanwhile, the light-emitting diode 100 may further include a second blocking layer (not illustrated) disposed between the light-emitting layer 50 and the second electrode 60.

The second blocking layer may be a hole blocking layer (HBL) which is disposed between the light-emitting layer 50 and the second electrode 60, specifically, the light-emitting layer 50 and the electron transporting layer, and thus, prevents holes from flowing into the electron transporting layer via the light-emitting layer 50 from the first electrode 20. Further, the second blocking layer may be an exciton blocking layer which prevents an exciton formed in the light-emitting layer 50 from being diffused in a direction of the second electrode 60, and thus being non-radiatively decayed.

When the thickness of the second blocking layer is adjusted so as to be suitable for the resonant length of the light-emitting diode 100, the light-emitting efficiency may be increased, and the thickness may be adjusted such that the exciton may be formed in the central portion of the light-emitting layer 50 other than the interface between the light-emitting layer 50 and another layer.

Figure 2:
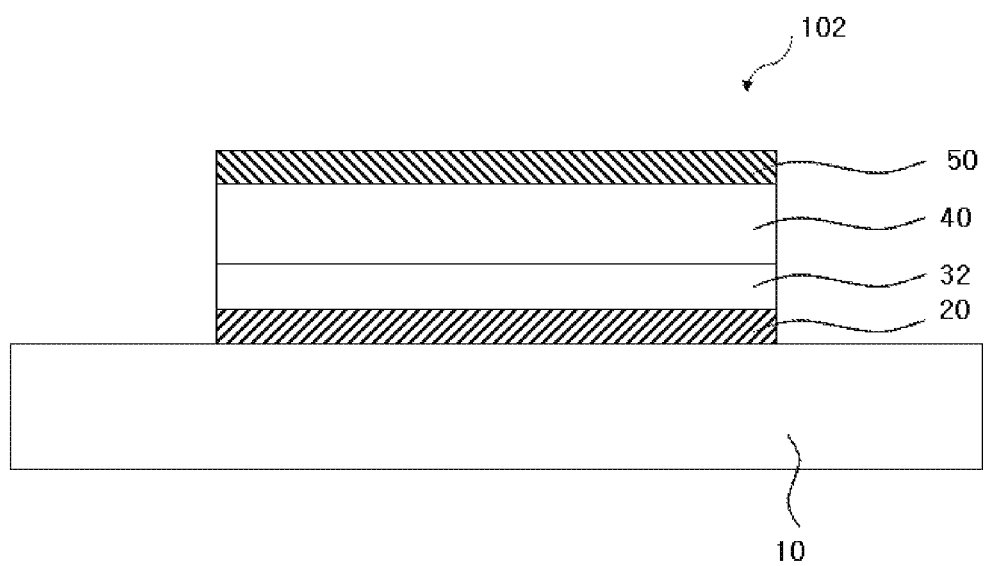
FIG. 2 is a cross-sectional view for describing a light-emitting diode according to another exemplary embodiment of the present invention.

FIG. 2 is a cross-sectional view for describing a light-emitting diode according to another exemplary embodiment of the present invention.

Referring to FIG. 2, a light-emitting diode 102 includes a first electrode 20, a hole transportable layer 32, a blocking layer 40, a light-emitting layer 50, and a second electrode 60, which are formed on a base substrate 10. Except for the hole transportable layer 32, the other constituent elements are substantially the same as those described in FIG. 1, and thus the overlapping description thereof will be omitted.

The hole transportable layer 32 includes the compound represented by Chemical Formula 18 and a P-type dopant. Since a compound included in the hole transportable layer 32 is substantially the same as that described above, the overlapping specific description thereof will be omitted.

The P-type dopant may include a P-type organic dopant and/or a P-type inorganic dopant.

Specific examples of the P-type organic dopant include compounds represented by the following Chemical Formulae 24 to 28, hexadecafluorophthalocyanine (F16CuPc), 11,11,12,12-tetracyanonaphtho-2,6-quinodimethane (TNAP), 3,6-difluoro-2,5,7,7,8,8-hexacyano-quinodimethane (F2-HCNQ), or tetracyanoquinodimethane (TCNQ), and the like. These may be used either alone or in combination of two or more thereof.

[Chemical Formula 24]

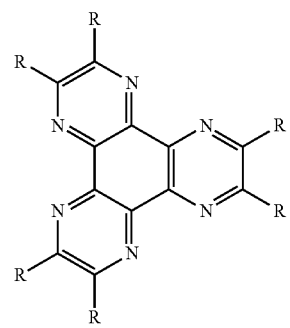

In the Chemical Formula, R may represent a cyano group, a sulfone group, a sulfoxide group, a sulfonamide group, a sulfonate group, a nitro group, or a trifluoromethyl group.

[Chemical Formula 25]

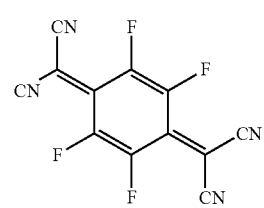

[Chemical Formula 26]

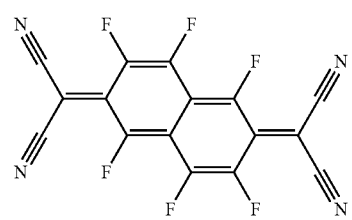

-continued

[Chemical Formula 27]

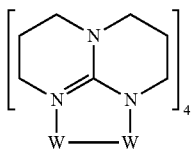

[Chemical Formula 28]

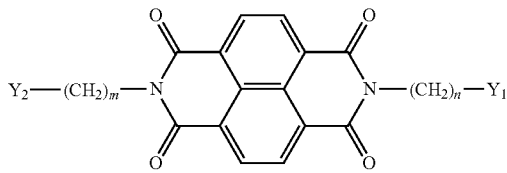

In the Chemical Formula, m and n each independently represent an integer of 1 to 5, and $Y_1$ and $Y_2$ may each independently represent an aryl group having 6 to 30 carbon atoms, or a heteroaryl group having 2 to 20 carbon atoms. In this case, in the Chemical Formula, hydrogen of the aryl group or heteroaryl group represented by $Y_1$ and $Y_2$ may be unsubstituted or substituted with an alkyl group having 1 to 5 carbon atoms, an alkoxy group having 1 to 5 carbon atoms, or a hydroxyl group, and hydrogens of substituted or unsubstituted $Y_1$ and $Y_2$ may be each independently unsubstituted or substituted with a halogen group.

For example, the compound represented by Chemical Formula 28 may include a compound represented by the following Chemical Formula 28a or the following Chemical Formula 28b.

[Chemical Formula 28a]

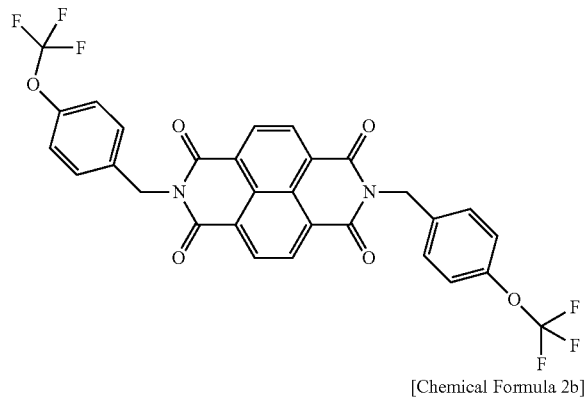

[Chemical Formula 2b]

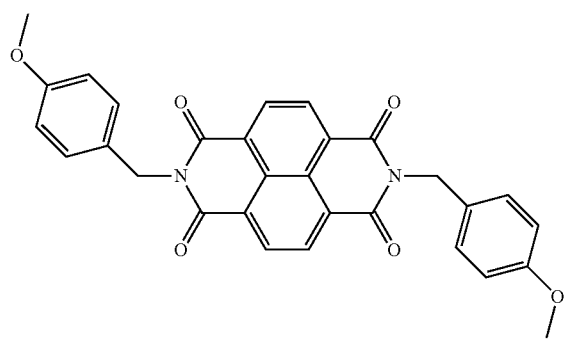

Examples of the P-type inorganic dopant include metal oxide or metal halide, and the like. Specific examples of the P-type inorganic dopant include $MoO_3$, $V_2O_5$, $WO_3$, $SnO_2$, $ZnO$, $MnO_2$, $CoO_2$, $ReO_3$, $TiO_2$, $FeCl_3$, $SbCl_5$ or $MgF_2$, and the like. These may be used either alone or in combination of two or more thereof.

The content of the P-type dopant may be about 0.5 part by weight to about 20 parts by weight based on 100 parts by weight of the compound according to the present invention, which is a hole transport compound. For example, the content of the P-type dopant may be about 0.5 part by weight to about 15 parts by weight, or about 0.5 part by weight to about 5 parts by weight based on 100 parts by weight of the hole transport compound. In contrast, the content of the P-type dopant may be about 1 part by weight to about 10 parts by weight, about 1 part by weight to about 5 parts by weight, about 1.5 parts by weight to about 6 parts by weight, or about 2 parts by weight to about 5 parts by weight, based on 100 parts by weight of the hole transport compound.

When the content of the P-type dopant is about 0.5 part by weight to about 20 parts by weight based on 100 parts by weight of the hole transport compound, the P-type dopant may prevent an excessive leakage current from being generated without degrading physical properties of the hole transport compound. In addition, the energy barrier at the interface with each of the upper and lower layers which are brought in contact with the hole transportable layer 32 may be reduced by the P-type dopant.

Even though not illustrated in the drawing, the light-emitting diode 102 may further include an electron transporting layer, an electron injecting layer, and/or a second blocking layer. Since the layers are substantially the same as those described in the light-emitting diode 100 of FIG. 1, the specific description thereof will be omitted.

Meanwhile, the light-emitting diode 100 illustrated in FIG. 1 may further include an interlayer (not illustrated). The interlayer may be disposed between the first electrode 20 and the hole transportable layer 30 of FIG. 1, and may be formed of the compound used as the P-type dopant described in FIG. 2.

Figure 3:
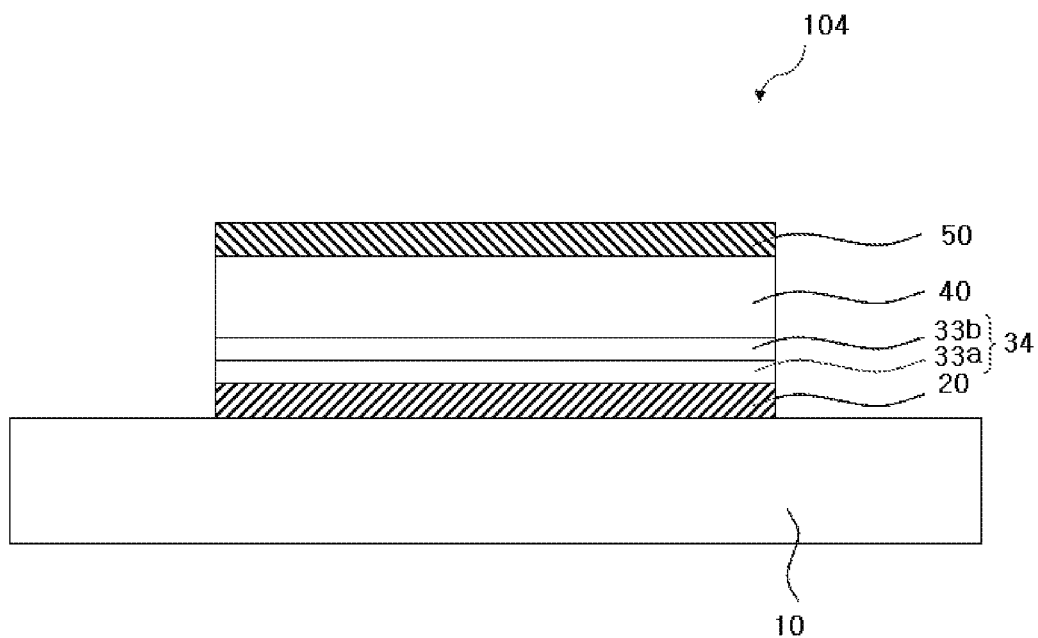
FIG. 3 is a cross-sectional view for describing a light-emitting diode according to still another exemplary embodiment of the present invention.

Referring to FIG. 3, a light-emitting diode 104 includes a first electrode 20, a hole transport layer 34, a blocking layer 40, a light-emitting layer 50, and a second electrode 60, which are formed on a base substrate 10. Except for the hole transportable layer 34, the other constituent elements are substantially the same as those described in FIG. 1, and thus the overlapping description thereof will be omitted.

The hole transportable layer 34 includes a first layer 33a brought in contact with the first electrode 20 and a second layer 33b disposed between the first layer 33a and the blocking layer 40. That is, the hole transportable layer 34 may have a two-layer structure. Further, the hole transportable layer 34 may have a multi-layer structure having two or more layers, which includes the first and second layers 33a and 33b.

The first and second layers 33a and 33b may include the same kind of hole transport compound. Components of the hole transport compound to be included in the first layer 33a and the second layer 33b are made identical to each other, so as to reduce physical and chemical defects which may be generated at the interface between different species materials, thereby facilitating injection of holes into the light-emitting layer. In another aspect, when the same host material is used for the first layer 33a and the second layer 33b, there is an advantage in that the first layer 33a and the second layer 33b may be continuously formed within one chamber, so that the manufacturing process may be simplified and the manufacturing time may be shortened. Furthermore, physical properties such as the glass transition temperature between the layers adjacent to each other become similar to each other, so that there is also an advantage in that durability of the diode may be increased.

The first layer 33a includes the compound according to the present invention, which is represented by Chemical Formula 18 as the hole transport compound, and a P-type dopant. Except for the thickness, the first layer 33a is substantially the same as the hole transportable layer 32 described in FIG. 2. Therefore, the overlapping description thereof will be omitted.

The second layer 33b includes the compound represented by Chemical Formula 18 as the hole transport compound, but the hole transport compound which constitutes the second layer 33b may be the same as the hole transport compound which constitutes the first layer 33a. Since the second layer 33b is also substantially the same as the hole transportable layer 30 described in FIG. 1 except for the thickness, the overlapping detailed description thereof will be omitted.

In contrast, the first and second layers 33a and 33b may include a different kind of hole transport compound. The hole transport compound, which constitutes the first and second layers 33a and 33b, is the compound represented by Chemical Formula 18, but one or more of $R_{13}$, $R_{14}$, $L_g$, $Ar_c$, and $Ar_d$ may be each independently different from each other. In this case, the compound, which constitutes each of the first and second layers 33a and 33b, may be selected so as to have a HOMO value for efficiently transferring holes to the light-emitting layer 50.

Additionally, the second layer 33b may further include a P-type dopant together with the hole transport compound. The kinds of P-type dopants doped in the first layer 33a and the second layer 33b may be different from each other, and an amount of doping may vary even though the same kind thereof is used. For example, the content (P1) of the P-type dopant doped in the first layer 33a and the content (P2) of the P-type dopant doped in the second layer 33b may satisfy the relationship of the following Equation 1.

$$P1/P2 \geq 1 \quad \text{[Equation 1]}$$

In Equation 1,
"P1" is a content of the P-type dopant doped in the first layer 33a based on 100 parts by weight of the hole transport compound, and "P2" is a content of the P-type dopant doped in the second layer 33b based on 100 parts by weight of the hole transport compound.

For example, the content of the P-type dopant doped in the first layer 33a may range from 0.3 to 20 parts by weight, 1 to 15 parts by weight, 2 to 10 parts by weight, or 4 to 6 parts by weight based on 100 parts by weight of the hole transport compound. Further, the content of the P-type dopant doped in the second layer 33b may range from 0.3 to 20 parts by weight, 0.5 to 10 parts by weight, 1 to 8 parts by weight, or 2 to 4 parts by weight based on 100 parts by weight of the hole transport compound.

In addition, even though not illustrated in the drawing, the light-emitting diode 104 may further include an electron transporting layer, an electron injecting layer, and/or a second blocking layer. Since the layers are substantially the same as those described in the light-emitting diode 100 of FIG. 1, the specific description thereof will be omitted.

Each of the light-emitting diodes 100, 102, and 104 described above includes the blocking layer 40 including the compound represented by Chemical Formula 1, and thus the light-emitting diodes 100, 102, and 104 may have excellent thermal stability, and simultaneously, the light-emitting efficiency thereof may be enhanced and the lifespan may be increased.

FIGS. 1 to 3 illustrate that the light-emitting diodes 100, 102, and 104 are directly formed on the base substrate 10, but a thin film transistor may be disposed as a driving diode which drives pixels between the first electrode 20 of each of the light-emitting diodes 100, 102, and 104 and the base substrate 10. In this case, the first electrode 20 may become a pixel electrode connected to the thin film transistor. When the first electrode 20 is a pixel electrode, the first electrodes 20 are disposed spaced apart from each other in each of a plurality of pixels and a partition wall pattern formed along the edge of the first electrode 20 is formed on the base substrate 10, so that layers to be stacked on the first electrode 20 disposed on the pixels adjacent to each other may be isolated from each other. That is, even though not illustrated in the drawing, the light-emitting diodes 100, 102, and 104 may be used in a display device which displays an image without a backlight.

Furthermore, the light-emitting diodes 100, 102, and 104 may be used as a lighting device.

As described above, the light-emitting diodes 100, 102, and 104 exemplified in the present invention may be used in the electronic apparatuses with various forms, and examples of the electronic apparatus include a display device or a lighting device, and the like.

EXAMPLES

Hereinafter, novel compounds according the present invention will be described in more detail through the specific Examples according to the present invention. The Examples to be exemplified below are only provided for the detailed description of the invention, but are not intended to limit the right scope thereby.

Preparation Example 1

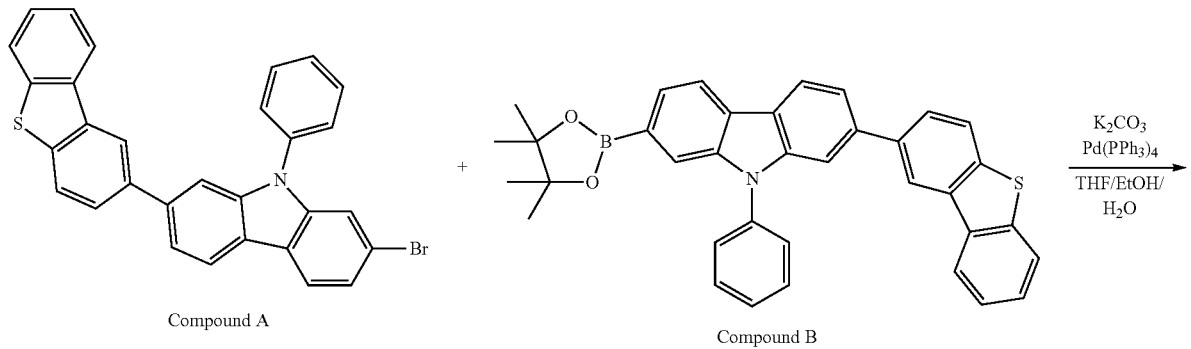

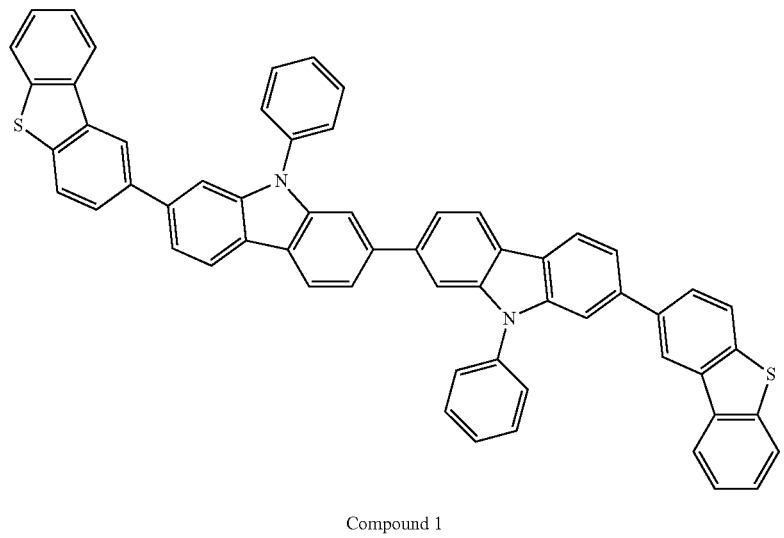

Compound 1

A 1 L three-neck round-bottom flask was filled with nitrogen, and then Compound A (67.4 mmol, 34.0 g), Compound B (74.1 mmol, 40.9 g), 340 mL of tetrahydrofuran (THF), and 170 mL of ethanol (EtOH) were put thereinto, and the resulting mixture was stirred for 30 minutes. Further, potassium carbonate ($K_2CO_3$) (269.6 mmol, 37.3 g) was dissolved in 170 mL of water ($H_2O$), and then the resulting solution was added to the 1 L three-neck round-bottom flask. Subsequently, tetrakis(triphenylphosphine)palladium (Pd(PPh$_3$)$_4$) (2.7 mmol, 3.1 g) was added to the 1 L three-neck round-bottom flask, and then the resulting mixture was refluxed for 6 hours while the light is blocked. The reaction mixture was cooled, and then extracted by using ethyl acetate (EA) and distilled water and concentrated, the concentrate was dissolved in 170 mL of tetrahydrofuran (THF), and the resulting solution was put into 1,700 mL of methanol and stirred for 20 minutes, and then filtered, thereby obtaining 40.1 g of a pale gray solid Compound 1 (yield 70%).

MALDI-TOF: m/z=848.2359 ($C_{60}H_{36}N_2S_2$=848.23)

Preparation Example 2

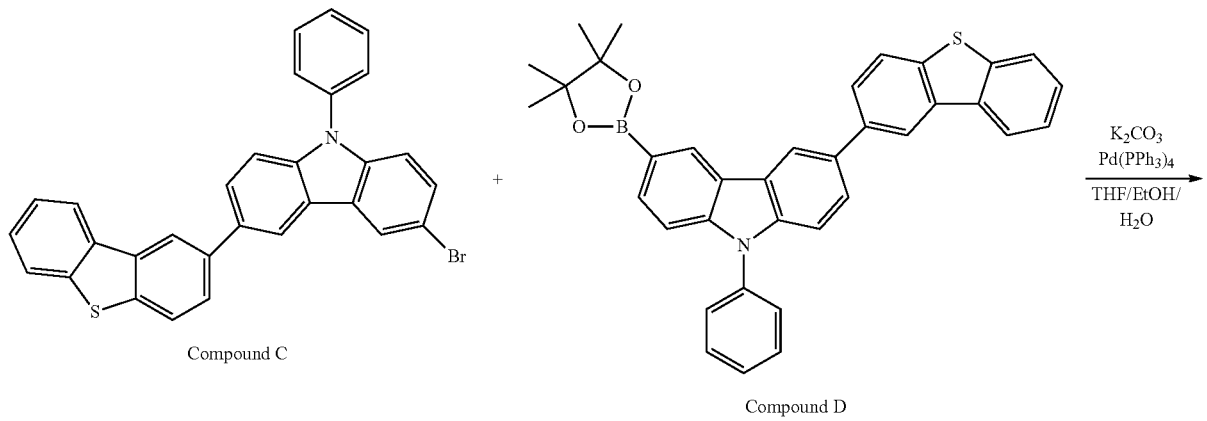

Compound C + Compound D →(K₂CO₃, Pd(PPh₃)₄, THF/EtOH/H₂O)

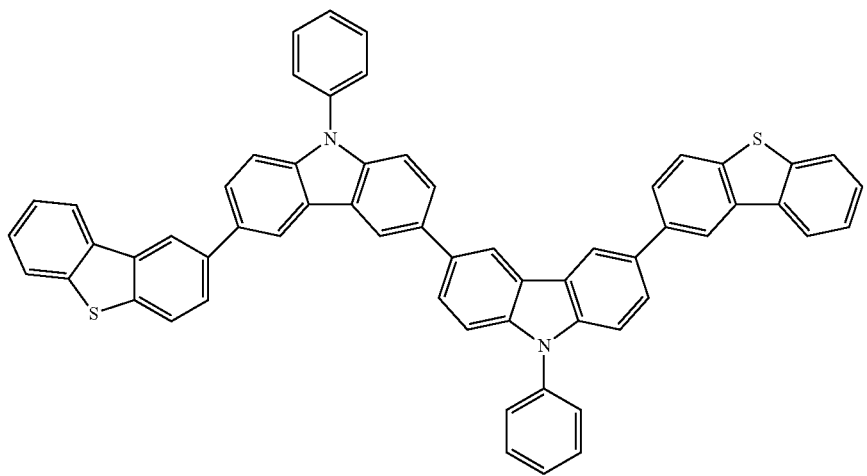

Compound 2

A 1 L three-neck round-bottom flask was filled with nitrogen, and then Compound C (19.8 mmol, 10.0 g), Compound D (21.8 mmol, 12.0 g), 100 mL of tetrahydrofuran (THF), and 50 mL of ethanol (EtOH) were put thereinto, and the resulting mixture was stirred for 30 minutes. Further, potassium carbonate ($K_2CO_3$) (79.3 mmol, 11.0 g) was dissolved in 50 mL of water ($H_2O$), and then the resulting solution was added to the 1 L three-neck round-bottom flask. Subsequently, tetrakis(triphenylphosphine) palladium (Pd(PPh₃)₄) (0.8 mmol, 0.9 g) was added to the 1 L three-neck round-bottom flask, and then the resulting mixture was refluxed for 6 hours while the light is blocked. The reaction mixture was cooled, and then extracted by using ethyl acetate (EA) and distilled water and concentrated, the concentrate was dissolved in 50 mL of tetrahydrofuran (THF), and the resulting solution was put into 500 mL of methanol and stirred for 20 minutes, and then filtered, thereby obtaining 13.5 g of a pale gray solid Compound 2 (yield 80%).

MALDI-TOF: m/z=848.2349 ($C_{60}H_{36}N_2S_2$=848.23)

Preparation Example 3

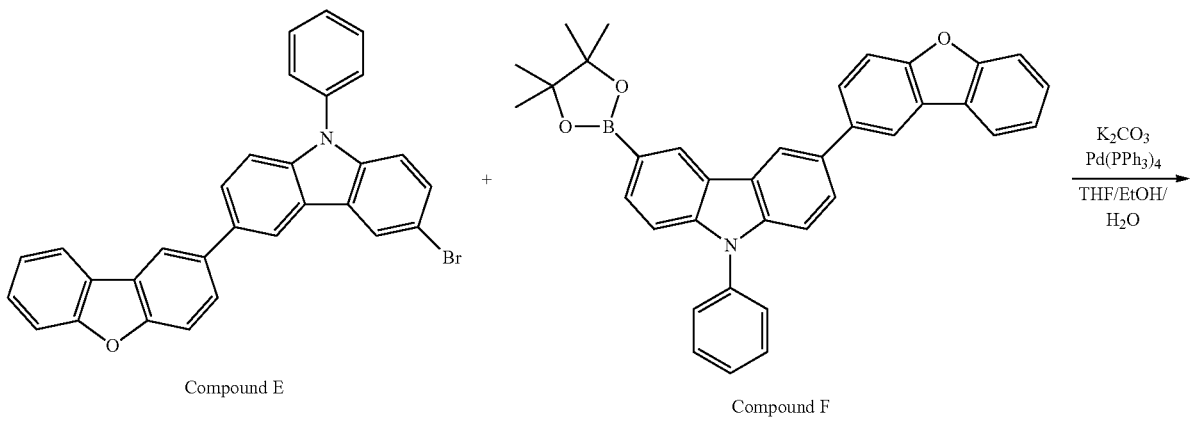

Compound E + Compound F → (K₂CO₃, Pd(PPh₃)₄, THF/EtOH/H₂O)

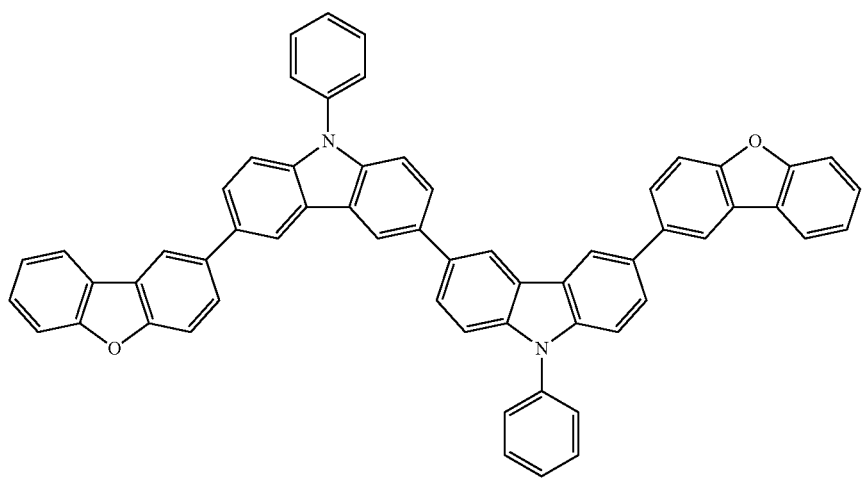

Compound 3

A 1 L three-neck round-bottom flask was filled with nitrogen, and then Compound E (41.0 mmol, 20.0 g), Compound F (45.0 mmol, 24.1 g), 200 mL of tetrahydrofuran (THF), and 100 mL of ethanol (EtOH) were put thereinto, and the resulting mixture was stirred for 30 minutes. Further, potassium carbonate (K₂CO₃) (163.8 mmol, 22.6 g) was dissolved in 100 mL of water (H₂O), and then the resulting solution was added to the 1 L three-neck round-bottom flask. Subsequently, tetrakis(triphenylphosphine)palladium (Pd(PPh₃)₄) (1.6 mmol, 1.9 g) was added to the 1 L three-neck round-bottom flask, and then the resulting mixture was refluxed for 6 hours while the light is blocked. The reaction mixture was cooled, and then extracted by using ethyl acetate (EA) and distilled water and concentrated, the concentrate was dissolved in 100 mL of tetrahydrofuran (THF), and the resulting solution was put into 1,000 mL of methanol and stirred for 20 minutes, and then filtered, thereby obtaining 23.4 g of a pale gray solid Compound 3 (yield 70%).

MALDI-TOF: m/z=816.2819 ($C_{60}H_{36}N_2O_2$=816.28)

Preparation Example 4

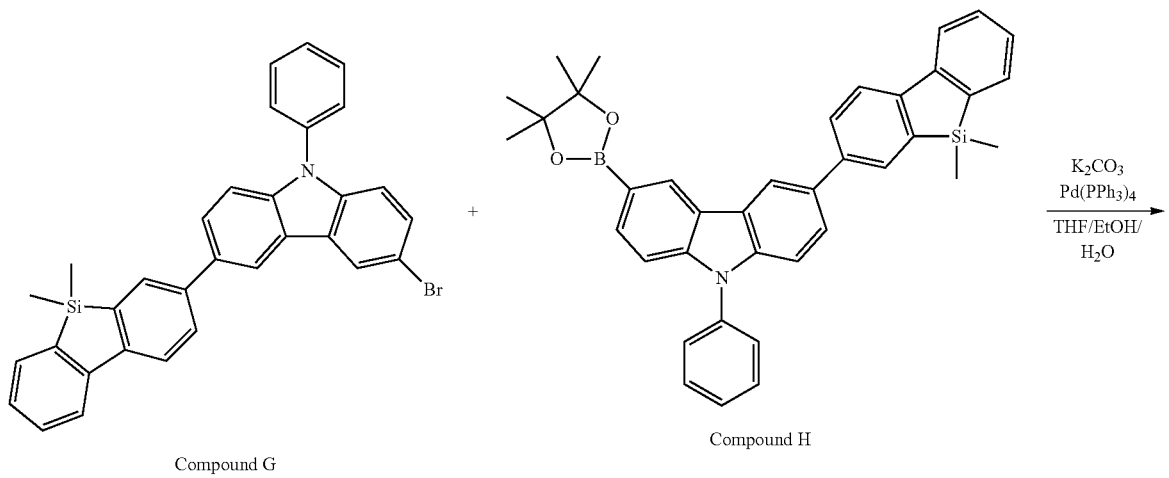

Compound G + Compound H

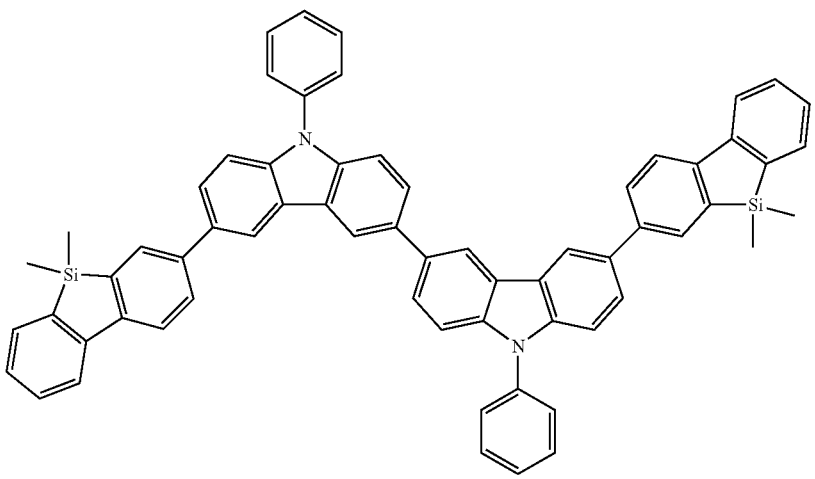

Compound 4

A 1 L three-neck round-bottom flask was filled with nitrogen, and then Compound G (47.1 mmol, 25.0 g), Compound H (51.8 mmol, 29.9 g), 250 mL of tetrahydrofuran (THF), and 125 mL of ethanol (EtOH) were put thereinto, and the resulting mixture was stirred for 30 minutes. Further, potassium carbonate ($K_2CO_3$) (188.5 mmol, 26.0 g) was dissolved in 50 mL of water ($H_2O$), and then the resulting solution was added to the 1 L three-neck round-bottom flask. Subsequently, tetrakis(triphenylphosphine)palladium (Pd(PPh$_3$)$_4$) (1.9 mmol, 2.2 g) was added to the 1 L three-neck round-bottom flask, and then the resulting mixture was refluxed for 6 hours while the light is blocked. The reaction mixture was cooled, and then extracted by using ethyl acetate (EA) and distilled water and concentrated, the concentrate was dissolved in 125 mL of tetrahydrofuran (THF), and the resulting solution was put into 1,250 mL of methanol and stirred for 20 minutes, and then filtered, thereby obtaining 29.7 g of a pale gray solid Compound 5 (yield 70%).

MALDI-TOF: m/z=900.3419 ($C_{64}H_{48}N_2Si_2$=900.34)

Preparation Example 5

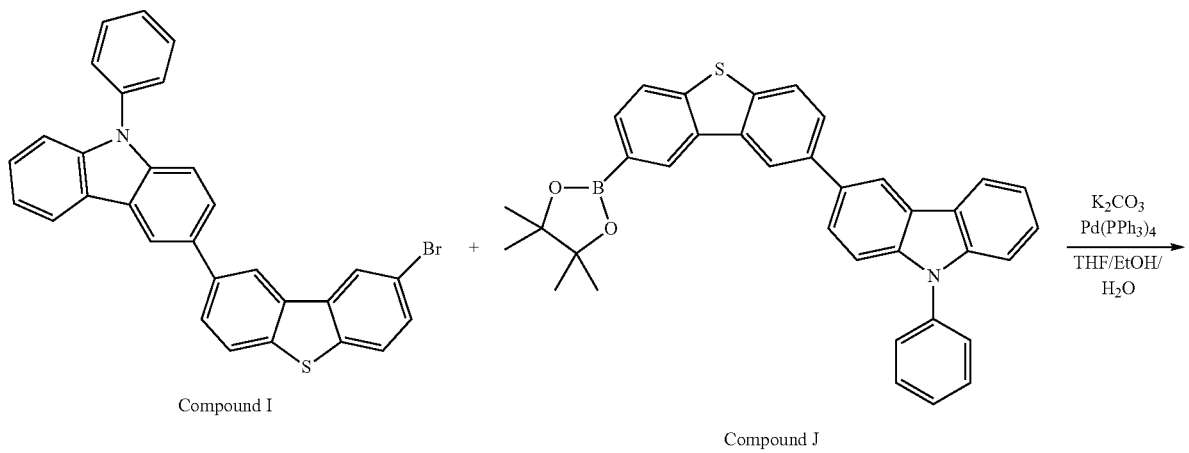

Compound I + Compound J

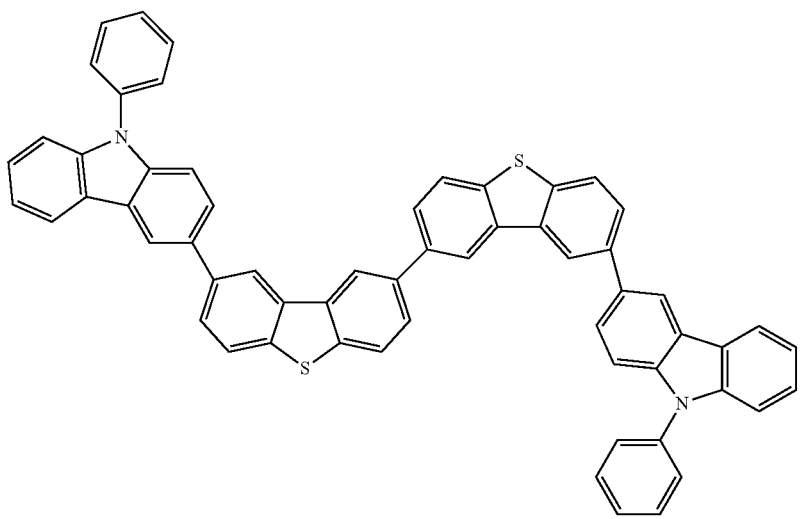

Compound 5

A 1 L three-neck round-bottom flask was filled with nitrogen, and then Compound I (15.9 mmol, 8.0 g), Compound J (17.4 mmol, 9.6 g), 80 mL of tetrahydrofuran (THF), and 40 mL of ethanol (EtOH) were put thereinto, and the resulting mixture was stirred for 30 minutes. Further, potassium carbonate ($K_2CO_3$) (63.4 mmol, 8.8 g) was dissolved in 40 mL of water ($H_2O$), and then the resulting solution was added to the 1 L three-neck round-bottom flask. Subsequently, tetrakis(triphenylphosphine)palladium (Pd($PPh_3$)$_4$) (0.6 mmol, 0.7 g) was added to the 1 L three-neck round-bottom flask, and then the resulting mixture was refluxed for 6 hours while the light is blocked. The reaction mixture was cooled, and then extracted by using ethyl acetate (EA) and distilled water and concentrated, the concentrate was dissolved in 40 mL of tetrahydrofuran (THF), and the resulting solution was put into 400 mL of methanol and stirred for 20 minutes, and then filtered, thereby obtaining 11.4 g of a pale gray solid Compound 5 (yield 85%).

MALDI-TOF: m/z=848.2354 ($C_{60}H_{36}N_2S_2$=848.23)

Preparation Example 6

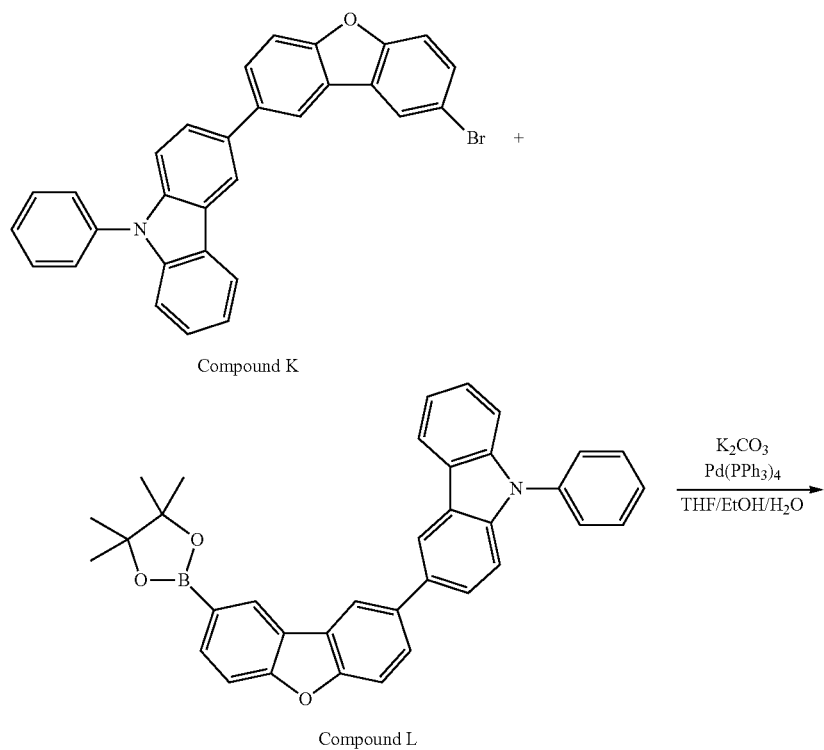

Compound K

Compound L

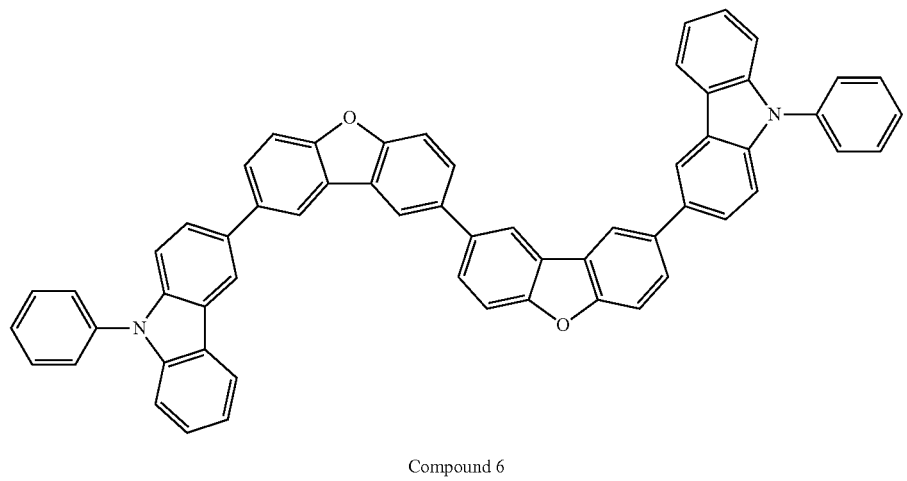

Compound 6

A 1 L three-neck round-bottom flask was filled with nitrogen, and then Compound K (61.4 mmol, 30.0 g), Compound L (67.6 mmol, 36.2 g), 300 mL of tetrahydrofuran (THF), and 150 mL of ethanol (EtOH) were put thereinto, and the resulting mixture was stirred for 30 minutes. Further, potassium carbonate ($K_2CO_3$) (245.7 mmol, 34.0 g) was dissolved in 150 mL of water ($H_2O$), and then the resulting solution was added to the 1 L three-neck round-bottom flask. Subsequently, tetrakis(triphenylphosphine)palladium ($Pd(PPh_3)_4$) (2.5 mmol, 2.8 g) was added to the 1 L three-neck round-bottom flask, and then the resulting mixture was refluxed for 6 hours while the light is blocked. The reaction mixture was cooled, and then extracted by using ethyl acetate (EA) and distilled water and concentrated, the concentrate was dissolved in 150 mL of tetrahydrofuran (THF), and the resulting solution was put into 1,500 mL of methanol and stirred for 20 minutes, and then filtered, thereby obtaining 35.1 g of a pale gray solid Compound 6 (yield 70%).

MALDI-TOF: m/z=816.2834 ($C_{60}H_{36}N_2O_2$=816.28)

Preparation Example 7

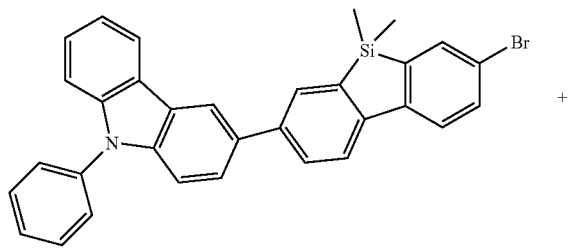

Compound M

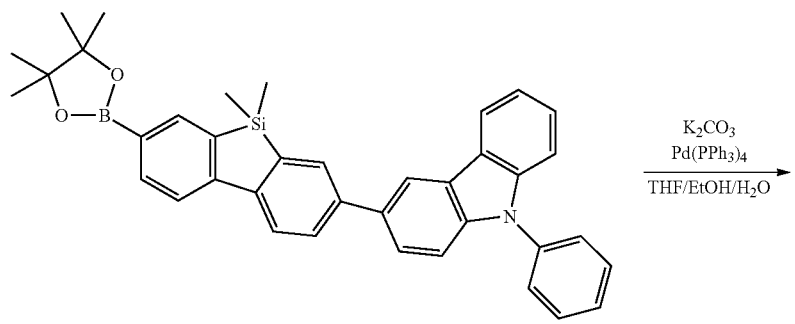

Compound N

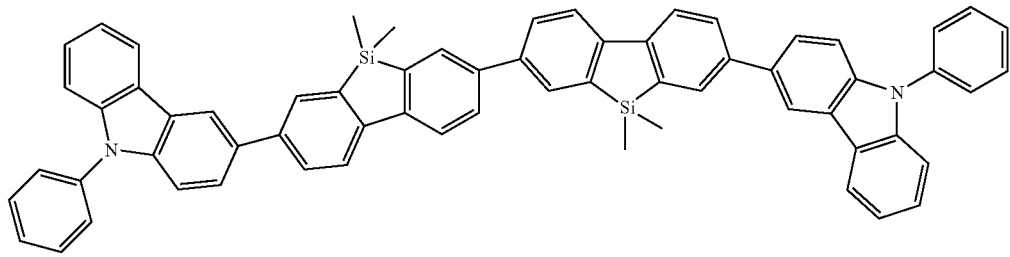

Compound 7

A 1 L three-neck round-bottom flask was filled with nitrogen, and then Compound M (47.1 mmol, 25.0 g), Compound N (51.8 mmol, 29.9 g), 250 mL of tetrahydrofuran (THF), and 125 mL of ethanol (EtOH) were put thereinto, and the resulting mixture was stirred for 30 minutes. Further, potassium carbonate ($K_2CO_3$) (188.5 mmol, 26.0 g) was dissolved in 125 mL of water ($H_2O$), and then the resulting solution was added to the 1 L three-neck round-bottom flask. Subsequently, tetrakis(triphenylphosphine)palladium (Pd(PPh$_3$)$_4$) (1.9 mmol, 2.2 g) was added to the 1 L three-neck round-bottom flask, and then the resulting mixture was refluxed for 6 hours while the light is blocked. The reaction mixture was cooled, and then extracted by using ethyl acetate (EA) and distilled water and concentrated, the concentrate was dissolved in 125 mL of tetrahydrofuran (THF), and the resulting solution was put into 1,250 mL of methanol and stirred for 20 minutes, and then filtered, thereby obtaining 29.7 g of a pale gray solid Compound 7 (yield 70%).

MALDI-TOF: m/z=900.3423 ($C_{64}H_{48}N_2Si_2$=900.34)

Preparation Example 8

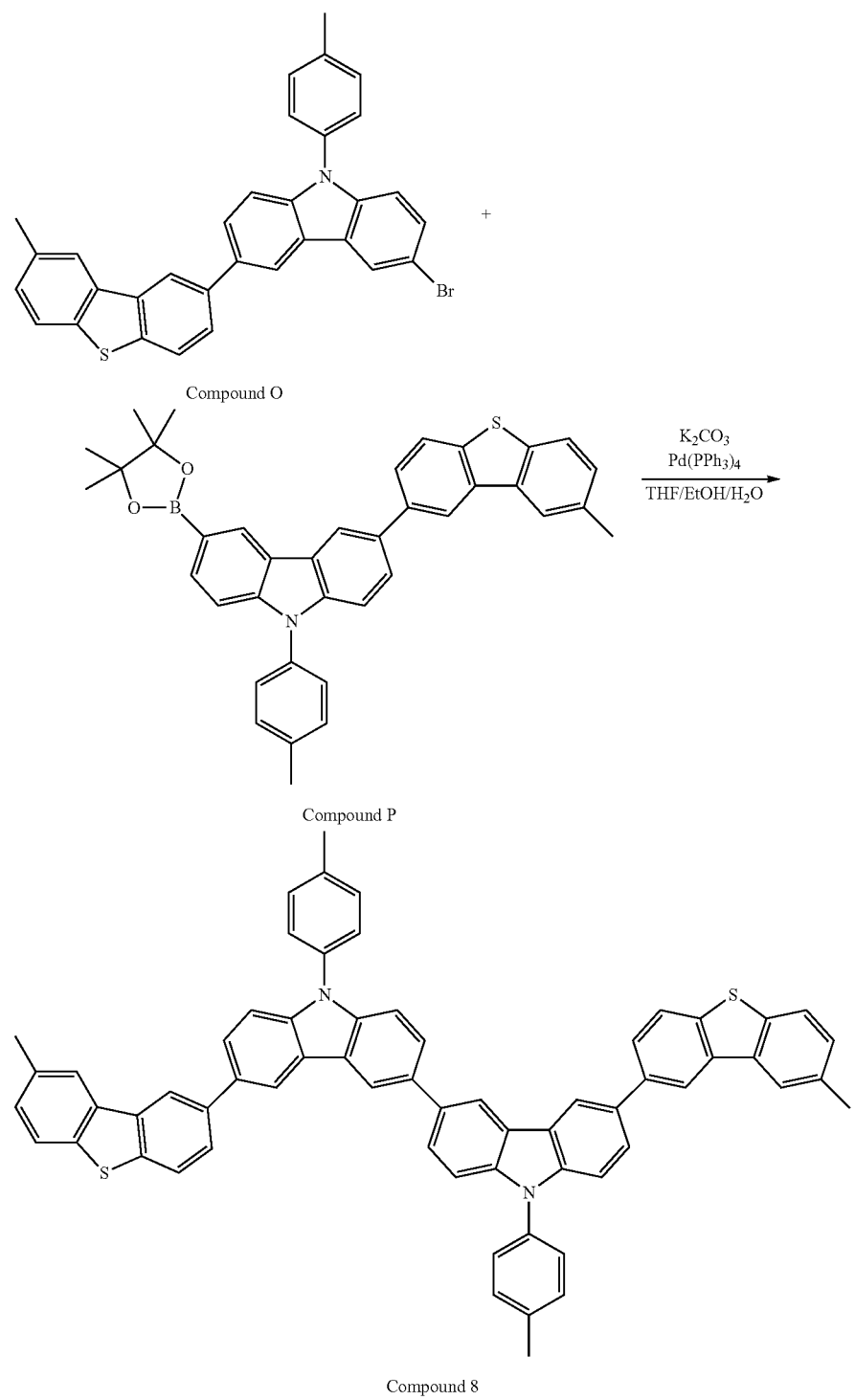

A 1 L three-neck round-bottom flask was filled with nitrogen, and then Compound 0 (37.6 mmol, 20.0 g), Compound P (41.3 mmol, 24.0 g), 200 mL of tetrahydrofuran (THF), and 100 mL of ethanol (EtOH) were put thereinto, and the resulting mixture was stirred for 30 minutes. Further, potassium carbonate ($K_2CO_3$) (150.2 mmol, 20.8 g) was dissolved in 100 mL of water ($H_2O$), and then the resulting solution was added to the 1 L three-neck round-bottom flask.

Subsequently, tetrakis(triphenylphosphine)palladium (Pd(PPh₃)₄) (0.8 mmol, 0.9 g) was added to the 1 L three-neck round-bottom flask, and then the resulting mixture was refluxed for 7 hours while the light is blocked. The reaction mixture was cooled, and then extracted by using ethyl acetate (EA) and distilled water and concentrated, the concentrate was dissolved in 100 mL of tetrahydrofuran (THF), and the resulting solution was put into 1 L of methanol and stirred for 30 minutes, and then filtered, thereby obtaining 28.2 g of a pale gray solid Compound 8 (yield 83%).

MALDI-TOF: m/z=904.6587 ($C_{64}H_{44}N_2S_2$=904.29)

Preparation Example 9

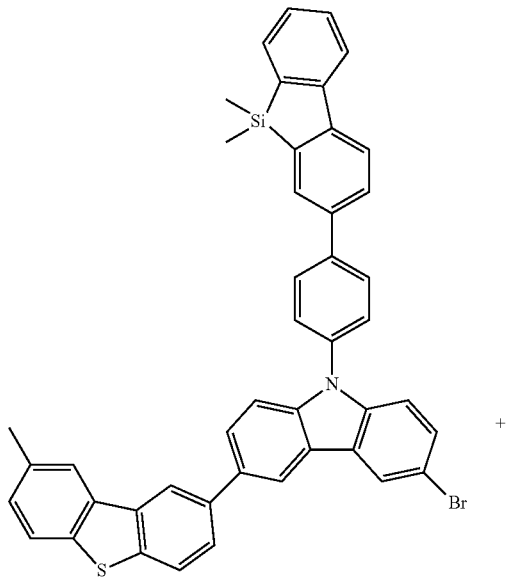

Compound Q

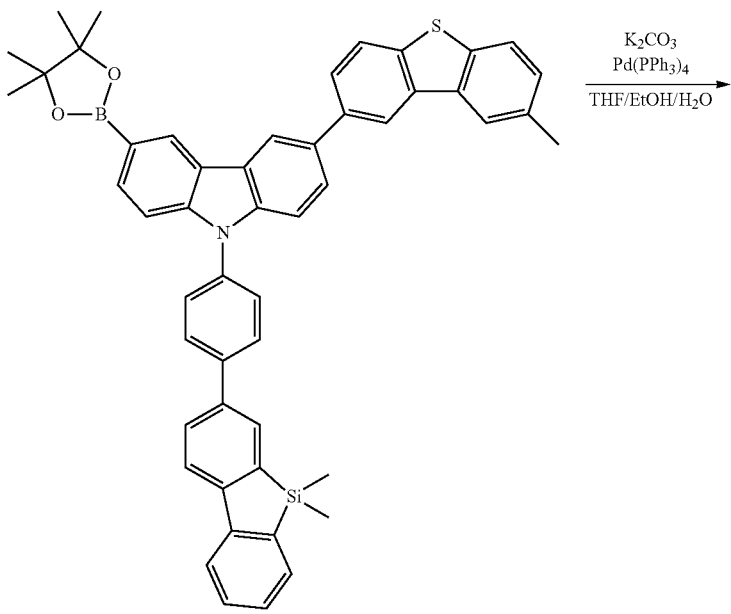

Compound R

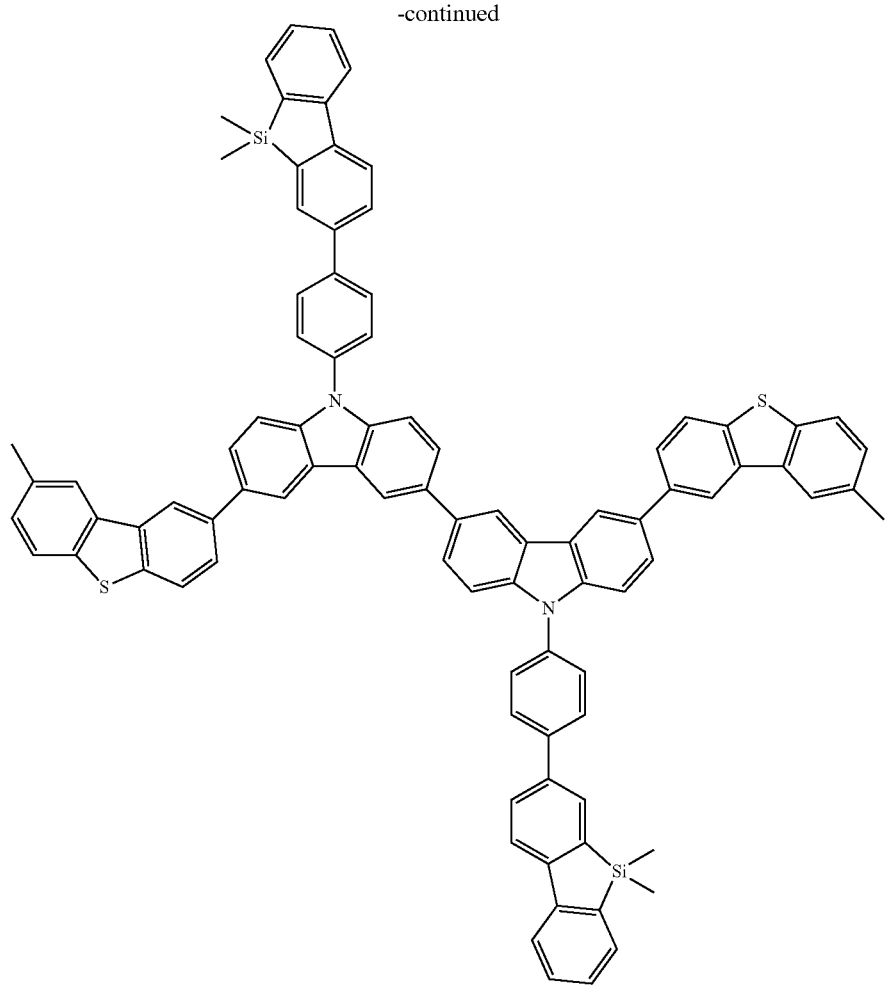

Compound 9

A 1 L three-neck round-bottom flask was filled with nitrogen, and then Compound Q (27.5 mmol, 20.0 g), Compound R (30.3 mmol, 23.4 g), 200 mL of tetrahydrofuran (THF), and 100 mL of ethanol (EtOH) were put thereinto, and the resulting mixture was stirred for 30 minutes. Further, potassium carbonate ($K_2CO_3$) (110.1 mmol, 15.2 g) was dissolved in 100 mL of water ($H_2O$), and then the resulting solution was added to the 1 L three-neck round-bottom flask. Subsequently, tetrakis(triphenylphosphine)palladium ($Pd(PPh_3)_4$) (0.7 mmol, 0.8 g) was added to the 1 L three-neck round-bottom flask, and then the resulting mixture was refluxed for 8 hours while the light is blocked. The reaction mixture was cooled, and then extracted by using ethyl acetate (EA) and distilled water and concentrated, the concentrate was dissolved in 100 mL of tetrahydrofuran (THF), and the resulting solution was put into 1 L of methanol and stirred for 40 minutes, and then filtered, thereby obtaining 27.8 g of a pale gray solid Compound 9 (yield 78%).

MALDI-TOF: m/z=1292.4312 ($C_{90}H_{64}N_2S_2Si_2$=1292.40)

Preparation Example 10

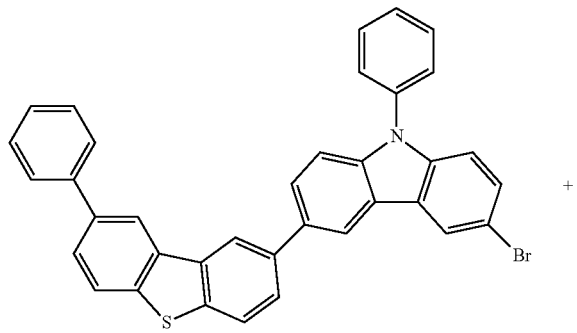

Compound S

-continued

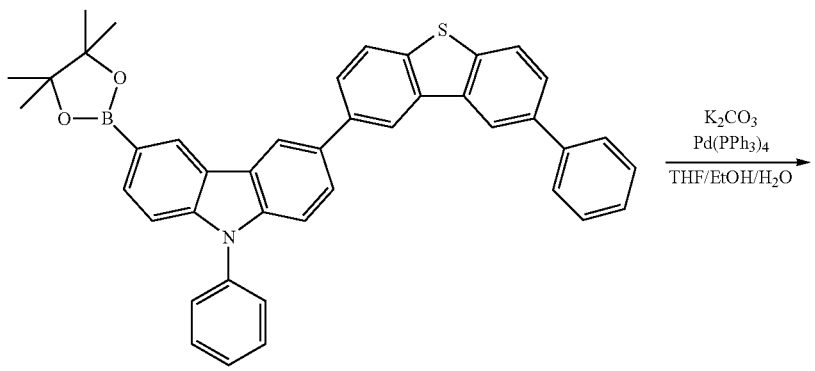

Compound T

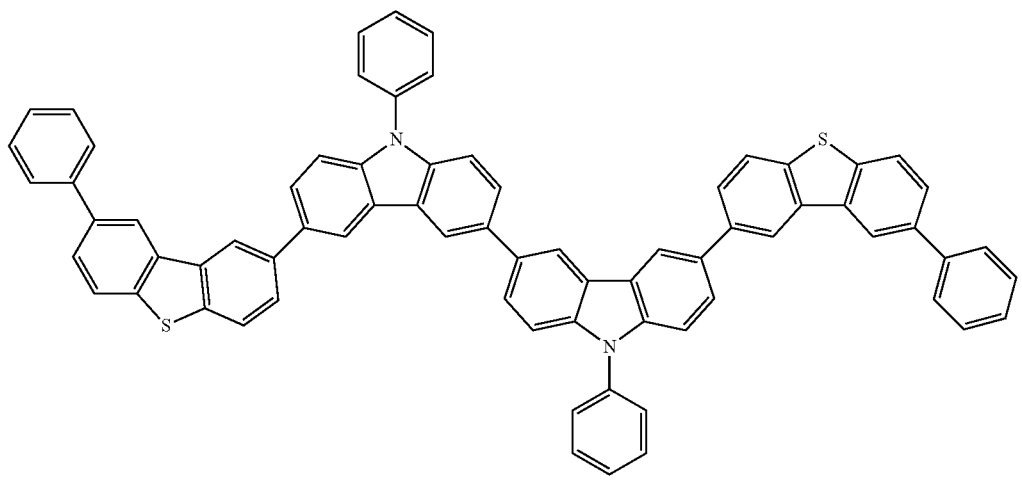

Compound 10

A 1 L three-neck round-bottom flask was filled with nitrogen, and then Compound S (34.5 mmol, 20.0 g), Compound T (37.9 mmol, 23.8 g), 200 mL of tetrahydrofuran (THF), and 100 mL of ethanol (EtOH) were put thereinto, and the resulting mixture was stirred for 30 minutes. Further, potassium carbonate ($K_2CO_3$) (137.8 mmol, 19.0 g) was dissolved in 100 mL of water ($H_2O$), and then the resulting solution was added to the 1 L three-neck round-bottom flask. Subsequently, tetrakis(triphenylphosphine)palladium (Pd(PPh$_3$)$_4$) (0.7 mmol, 0.8 g) was added to the 1 L three-neck round-bottom flask, and then the resulting mixture was refluxed for 6 hours while the light is blocked. The reaction mixture was cooled, and then extracted by using ethyl acetate (EA) and distilled water and concentrated, the concentrate was dissolved in 100 mL of tetrahydrofuran (THF), and the resulting solution was put into 1 L of methanol and stirred for 30 minutes, and then filtered, thereby obtaining 27.6 g of a pale gray solid Compound 10 (yield 80%).

MALDI-TOF: m/z=1000.5798 ($C_{72}H_{44}N_2S_2$=1000.29)

Preparation Example 11

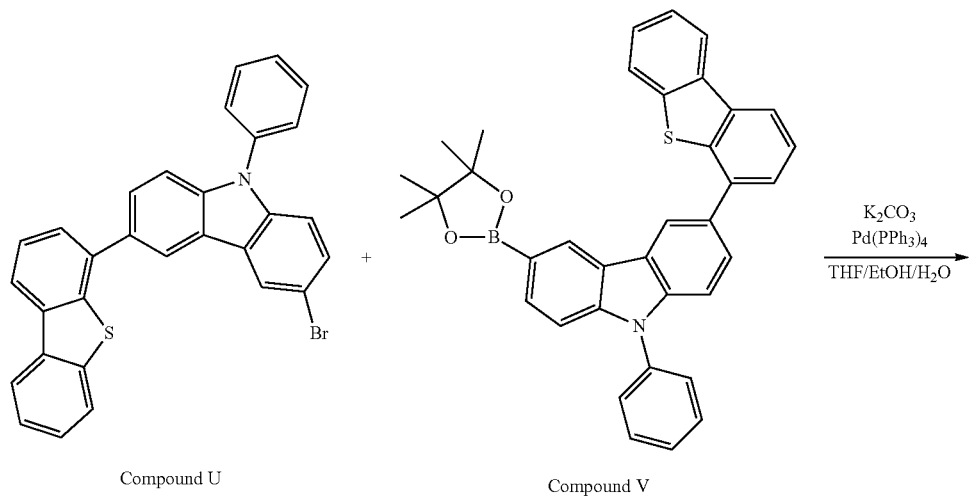

Compound U + Compound V → (K₂CO₃, Pd(PPh₃)₄, THF/EtOH/H₂O)

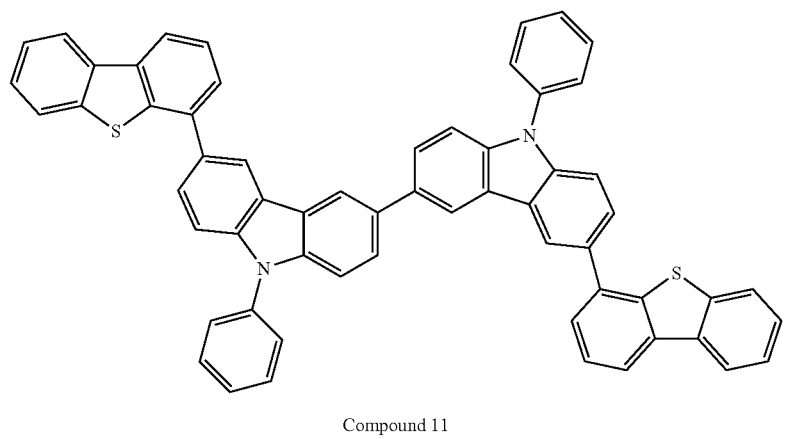

Compound 11

A 1 L three-neck round-bottom flask was filled with nitrogen, and then Compound U (19.8 mmol, 10.0 g), Compound V (21.8 mmol, 12.0 g), 100 mL of tetrahydrofuran (THF), and 50 mL of ethanol (EtOH) were put thereinto, and the resulting mixture was stirred for 20 minutes. Further, potassium carbonate ($K_2CO_3$) (79.3 mmol, 11.0 g) was dissolved in 50 mL of water ($H_2O$), and then the resulting solution was added to the 1 L three-neck round-bottom flask. Subsequently, tetrakis(triphenylphosphine)palladium (Pd(PPh₃)₄) (0.8 mmol, 0.9 g) was added to the 1 L three-neck round-bottom flask, and then the resulting mixture was refluxed for 5 hours while the light is blocked. The reaction mixture was cooled, and then extracted by using ethyl acetate (EA) and distilled water and concentrated, the concentrate was dissolved in 50 mL of tetrahydrofuran (THF), and the resulting solution was put into 500 mL of methanol and stirred for 30 minutes, and then filtered, thereby obtaining 13.5 g of a pale gray solid Compound 11 (yield 89%).

MALDI-TOF: m/z=848.2349 ($C_{60}H_{36}N_2S_2$=848.23)

Preparation Example 12

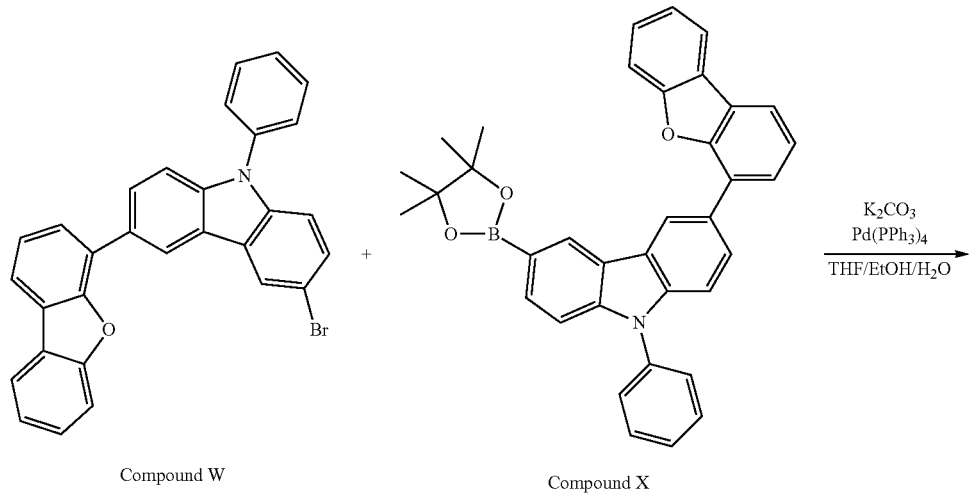

Compound W + Compound X

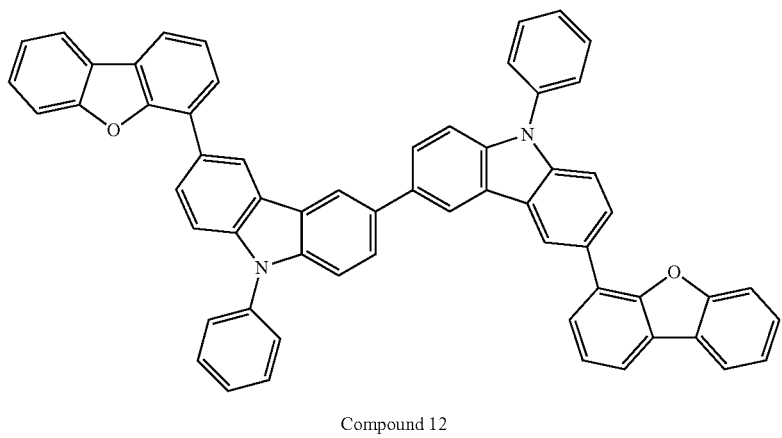

Compound 12

A 1 L three-neck round-bottom flask was filled with nitrogen, and then Compound W (41.0 mmol, 20.0 g), Compound X (45.0 mmol, 24.1 g), 200 mL of tetrahydrofuran (THF), and 100 mL of ethanol (EtOH) were put thereinto, and the resulting mixture was stirred for 30 minutes. Further, potassium carbonate ($K_2CO_3$) (163.8 mmol, 22.6 g) was dissolved in 100 mL of water ($H_2O$), and then the resulting solution was added to the 1 L three-neck round-bottom flask. Subsequently, tetrakis(triphenylphosphine)palladium (Pd(PPh$_3$)$_4$) (1.6 mmol, 1.9 g) was added to the 1 L three-neck round-bottom flask, and then the resulting mixture was refluxed for 7 hours while the light is blocked. The reaction mixture was cooled, and then extracted by using ethyl acetate (EA) and distilled water and concentrated, the concentrate was dissolved in 100 mL of tetrahydrofuran (THF), and the resulting solution was put into 1,000 mL of methanol and stirred for 30 minutes, and then filtered, thereby obtaining 28.7 g of a pale gray solid Compound 12 (yield 86%).

MALDI-TOF: m/z=816.2819 ($C_{60}H_{36}N_2O_2$=816.28)

Preparation Example 13

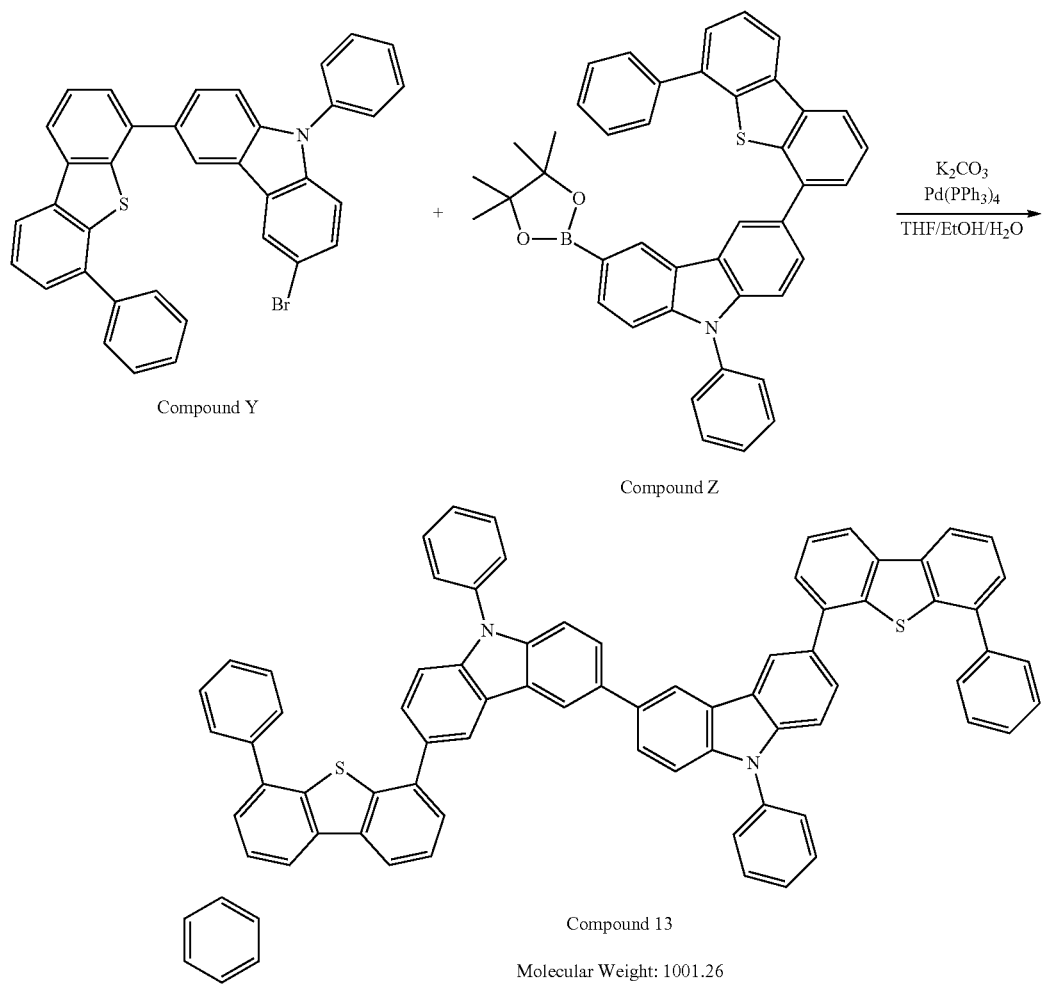

Compound 13

Molecular Weight: 1001.26

A 1 L three-neck round-bottom flask was filled with nitrogen, and then Compound Y (34.5 mmol, 20.0 g), Compound Z (37.9 mmol, 23.8 g), 200 mL of tetrahydrofuran (THF), and 100 mL of ethanol (EtOH) were put thereinto, and the resulting mixture was stirred for 20 minutes. Further, potassium carbonate ($K_2CO_3$) (137.8 mmol, 19.0 g) was dissolved in 100 mL of water ($H_2O$), and then the resulting solution was added to the 1 L three-neck round-bottom flask. Subsequently, tetrakis(triphenylphosphine)palladium ($Pd(PPh_3)_4$) (0.7 mmol, 0.8 g) was added to the 1 L three-neck round-bottom flask, and then the resulting mixture was refluxed for 5 hours while the light is blocked. The reaction mixture was cooled, and then extracted by using ethyl acetate (EA) and distilled water and concentrated, the concentrate was dissolved in 100 mL of tetrahydrofuran (THF), and the resulting solution was put into 1 L of methanol and stirred for 30 minutes, and then filtered, thereby obtaining 29.3 g of a pale gray solid Compound 13 (yield 85%).

MALDI-TOF: m/z=1000.5798 ($C_{72}H_{44}N_2S_2$=1000.29)

Example 1

Manufacture of Light-Emitting Diodes A-1 to A-13

A compound represented by the following Chemical Formula 29 as a host material was deposited at a rate of 1 Å/sec, and simultaneously, a P-type dopant (HAT-CN) represented by the following Chemical Formula 30 was co-evaporated at a ratio of about 3 parts by weight based on 100 parts by weight of the host material, on a first electrode formed of indium tin oxide (ITO), thereby forming a first layer having a thickness of 100 Å. The compound represented by Chemical Formula 29 was deposited to have a thickness of 300 Å on the first layer, thereby forming a second layer.

The compound according to Preparation Example 1 was deposited to have a thickness of 100 Å on the second layer, thereby forming a blocking layer.

A compound represented by the following Chemical Formula 31 and a compound represented by the following Chemical Formula 32 were co-evaporated at a weight ratio of 100:5 on the blocking layer, thereby forming a light-emitting layer having a thickness of about 200 Å.

And then, a compound represented by the following Chemical Formula 33 and a compound represented by the following Chemical Formula 34 were co-evaporated at a weight ratio of 50:50 on the light-emitting layer, thereby forming an electron transporting layer having a thickness of about 360 Å. Subsequently, an electron injecting layer having a thickness of about 5 Å was formed on the electron transporting layer by using a compound represented by the following Chemical Formula 34.

A second electrode using an aluminum thin film having a thickness of 1,000 Å was formed on the electron injecting layer.

[Chemical Formula 29]

[Chemical Formula 30]

[Chemical Formula 31]

[Chemical Formula 32]

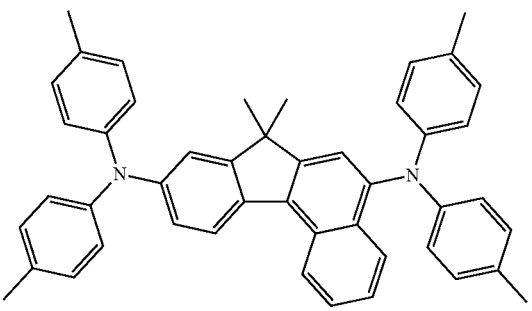

[Chemical Formula 33]

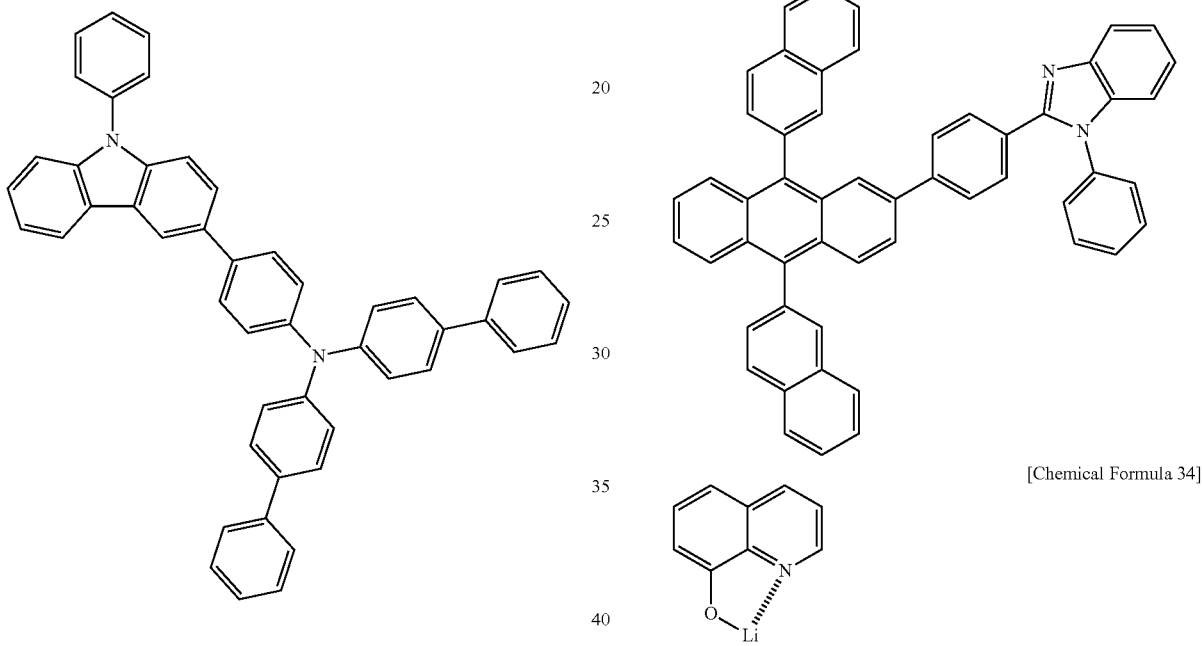

[Chemical Formula 34]

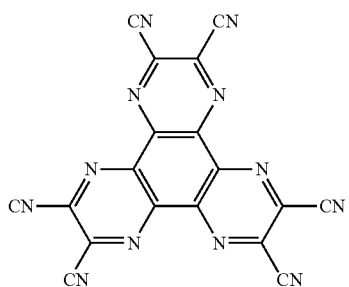

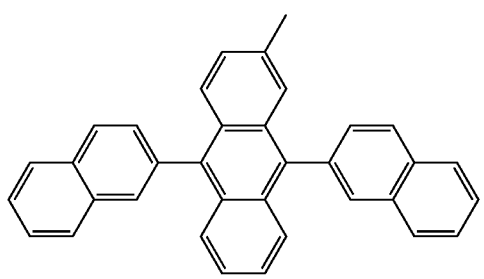

Light-emitting diode A-1 including the compound according to Preparation Example 1 of the present invention was manufactured by the above method. In addition, light-emitting diode A-2 to light-emitting diode A-13 were manufactured through a process which is substantially the same as the process of manufacturing light-emitting diode A-1, except that a blocking layer was formed by using each of the compounds according to Preparation Examples 2 to 13.

Example 2

Manufacture of Light-Emitting Diodes B-1 to B-13

A compound represented by Chemical Formula 35 as a host material was deposited at a rate of 1 Å/sec, and simultaneously, the P-type dopant (HAT-CN) represented by Chemical Formula 30 was co-evaporated at a ratio of about 3 parts by weight based on 100 parts by weight of the host material, on a first electrode formed of indium tin oxide (ITO), thereby forming a first layer having a thickness of 100 Å. The compound represented by Chemical Formula 35 was deposited to have a thickness of 300 Å on the first layer, thereby forming a second layer.

The compound according to Preparation Example 1 was deposited to have a thickness of 100 Å on the second layer, thereby forming a blocking layer.

A compound represented by Chemical Formula 36 and the compound represented by Chemical Formula 32 were co-evaporated at a weight ratio of 100:5 on the blocking layer, thereby forming a light-emitting layer having a thickness of about 200 Å.

And then, the compound represented by Chemical Formula 33 and the compound represented by Chemical Formula 34 were co-evaporated at a weight ratio of 50:50 on the light-emitting layer, thereby forming an electron transporting layer having a thickness of about 360 Å. Subsequently, an electron injecting layer having a thickness of about 5 Å was formed on the electron transporting layer by using the compound represented by Chemical Formula 34.

A second electrode using an aluminum thin film having a thickness of 1,000 Å was formed on the electron injecting layer.

[Chemical Formula 35]

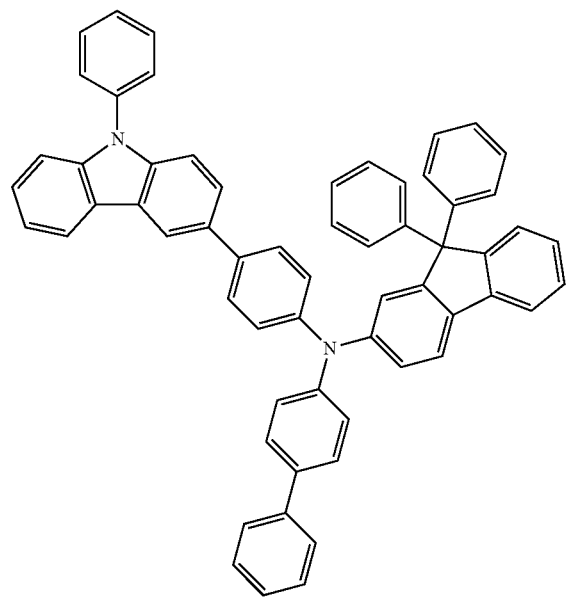

[Chemical Formula 36]

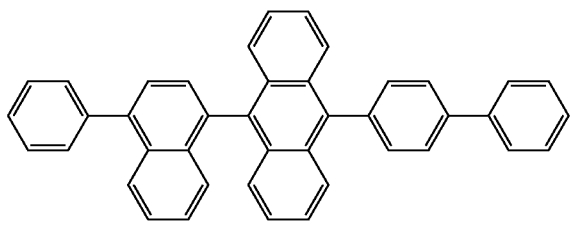

Light-emitting diode B-1 including the compound according to Preparation Example 1 of the present invention was manufactured by the above method.

In addition, light-emitting diode B-2 to light-emitting diode B-13 were manufactured through a process which is substantially the same as the process of manufacturing light-emitting diode B-1, except that a blocking layer was formed by using each of the compounds according to Preparation Examples 2 to 13.

Example 3

Manufacture of Light-Emitting Diodes C-1 to C-13

A compound represented by Chemical Formula 37 as a host material was deposited at a rate of 1 Å/sec, and simultaneously, the P-type dopant (HAT-CN) represented by Chemical Formula 30 was co-evaporated at a ratio of about 3 parts by weight based on 100 parts by weight of the host material, on a first electrode formed of indium tin oxide (ITO), thereby forming a first layer having a thickness of 100 Å. A compound represented by Chemical Formula 37 was deposited to have a thickness of 300 Å on the first layer, thereby forming a second layer.

The compound according to Preparation Example 1 was deposited to have a thickness of 100 Å on the second layer, thereby forming a blocking layer.

A compound represented by Chemical Formula 38 and the compound represented by Chemical Formula 32 were co-evaporated at a weight ratio of 100:5 on the blocking layer, thereby forming a light-emitting layer having a thickness of about 200 Å.

And then, the compound represented by Chemical Formula 33 and the compound represented by Chemical Formula 34 were co-evaporated at a weight ratio of 50:50 on the light-emitting layer, thereby forming an electron transporting layer having a thickness of about 360 Å. Subsequently, an electron injecting layer having a thickness of about 5 Å was formed on the electron transporting layer by using the compound represented by Chemical Formula 34.

A second electrode using an aluminum thin film having a thickness of 1,000 Å was formed on the electron injecting layer.

[Chemical Formula 37]

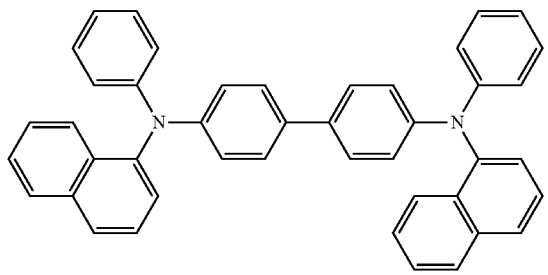

[Chemical Formula 38]

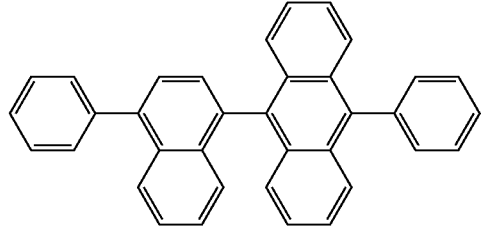

Light-emitting diode C-1 including the compound according to Preparation Example 1 of the present invention was manufactured by the above method.

In addition, light-emitting diode C-2 to light-emitting diode C-13 were manufactured through a process which is substantially the same as the process of manufacturing light-emitting diode C-1, except that a blocking layer was formed by using each of the compounds according to Preparation Examples 2 to 13.

Comparative Example 1

Comparative Diode 1 was manufactured through the process which is substantially the same as in Example 1, except that a separate blocking layer was not formed.

Comparative Example 2

Comparative Diode 2 was manufactured through the process which is substantially the same as in Example 2, except that a separate blocking layer was not formed.

Comparative Example 3

Comparative Diode 3 was manufactured through the process which is substantially the same as in Example 3, except that a separate blocking layer was not formed.

Comparative Example 4

Comparative Diode 4 was manufactured through the process which is substantially the same as in Example 1, except that a blocking layer was formed by using a compound represented by Chemical Formula 39.

[Chemical Formula 39]

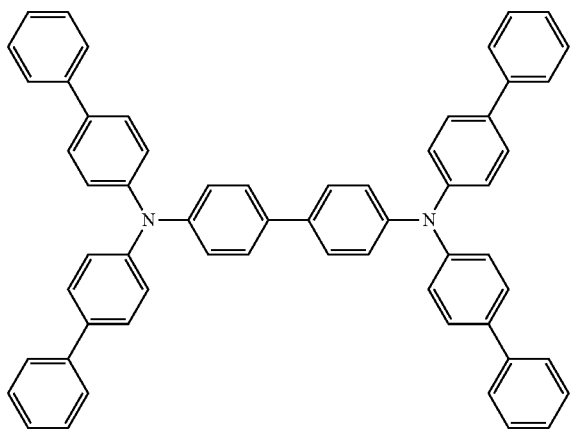

Comparative Example 5

Comparative Diode 5 was manufactured through the process which is substantially the same as in Example 2, except that a blocking layer was formed by using the compound represented by Chemical Formula 39.

Comparative Example 6

Comparative Diode 6 was manufactured through the process which is substantially the same as in Example 3, except that a blocking layer was formed by using the compound represented by Chemical Formula 39.

Experimental Example 1

Evaluation of Power Efficiency and Lifespan of Light-Emitting Diode

For each of light-emitting diodes A-1 to A-13 and comparative diodes 1 and 4, a sealant for UV curing was dispensed at the edge of a cover glass, to which a moisture absorbent (Getter) was attached, in a glove box under a nitrogen atmosphere, and then each of the light-emitting diodes was cohered to the cover glass, and the sealant was cured by irradiating UV light thereon. For each of light-emitting diodes A-1 to A-13 and comparative diodes 1 and 4 thus prepared above, the power efficiency was measured based on the value when the brightness was 1,000 cd/m². The unit of the result of measuring the power efficiency was lm/W. Further, the lifespan of each of light-emitting diodes A-1 to A-13 and comparative diodes 1 and 4 was measured by using a lifetime measurement device provided in a measurement oven which was maintained constantly at a temperature of 25° C. $T_{50}$ means a time for brightness of the light-emitting diode to become 50% as compared to the initial brightness, when the initial brightness of the light-emitting diode is 5,000 cd/m². The value for the lifespan may be converted into a lifespan which is expected in the case where the measurement is made under other measurement conditions based on the conversion equation publicly known to the person skilled in the art.

The measurement result is shown in Table 1.

TABLE 1

| Diode No. | Power efficiency [lm/W] | Lifespan ($T_{50}$[hr]) |
|---|---|---|
| Light-emitting diode A-1 | 6.3 | 219 |
| Light-emitting diode A-2 | 6.7 | 247 |
| Light-emitting diode A-3 | 6.6 | 239 |
| Light-emitting diode A-4 | 5.9 | 202 |
| Light-emitting diode A-5 | 6.1 | 201 |
| Light-emitting diode A-6 | 5.8 | 187 |
| Light-emitting diode A-7 | 5.6 | 178 |
| Light-emitting diode A-8 | 7.7 | 272 |
| Light-emitting diode A-9 | 7.0 | 255 |
| Light-emitting diode A-10 | 7.5 | 263 |
| Light-emitting diode A-11 | 6.7 | 251 |
| Light-emitting diode A-12 | 6.6 | 245 |
| Light-emitting diode A-13 | 7.6 | 269 |
| Comparative diode 1 | 4.3 | 128 |
| Comparative diode 4 | 5.1 | 155 |

Referring to Table 1, it can be seen that the power efficiencies of light-emitting diodes A-1 to A-13, which include the blocking layer formed of each of the compounds according to Preparation Examples 1 to 13 of the present invention, are 5.6 lm/W or more, and the average power efficiency is about 6.6 lm/W. As compared to the case where the power efficiency of comparative diode 1 is 4.3 lm/W and the power efficiency of comparative diode 4 is 5.1 lm/W, it can be seen that the power efficiencies of light-emitting diodes A-1 to A-13 according to the present invention have been significantly increased. For example, it can be seen that the power efficiency of light-emitting diode A-8 is increased by about 50% or more compared to that of comparative diode 4.

It is shown that the lifespans of light-emitting diodes A-1 to A-13 are 178 hours or more and the average diode lifespan thereof is about 233 hours, whereas the lifespans of comparative diodes 1 and 4 are 128 hours and 155 hours, respectively. Accordingly, it can be seen that the lifespans of light-emitting diodes A-1 to A-13 according to the present invention have been significantly increased compared to the lifespans of comparative diodes 1 and 4. For example, it can be seen that the lifespan of light-emitting diode A-8 is increased by about 75% or more compared to that of comparative diode 4.

In addition, it can be seen that the bonding position of the substituent which constitutes the compound applied to the light-emitting diodes may affect physical properties of the light-emitting diodes. For example, when the structures of the respective compounds (Compound 2 and Compound 11) used in light-emitting diode A-2 and light-emitting diode A-11 are compared to each other, it can be seen that the two structures are the same as each other, except that the bonding positions of the substituents substituted at both ends of each compound are different from each other. When physical properties of light-emitting diode A-2 and light-emitting diode A-11 are compared to each other, it is shown that the power efficiencies are at the equivalent level. However, it can be seen that the lifespan of light-emitting diode A-11 has been enhanced by about 1.6%. As a similar case, when light-emitting diode A-3 and light-emitting diode A-12 are compared to each other, the lifespan of light-emitting diode A-12 has been enhanced by about 2.5%. Furthermore, when light-emitting diode A-10 and light-emitting diode A-13 are compared to each other, it can be seen that the lifespan of light-emitting diode A-13 has been enhanced by about 2.3%.

Experimental Example 2

Measurement of Color Coordinate of Light-Emitting Diode

For each of light-emitting diodes A-1 to A-13 and comparative diodes 1 and 4, the color coordinates were compared and measured. The color coordinate was measured based on CIE 1931. The result is shown in Table 2.

TABLE 2

| Diode No. | Color Coordinate (x value) | Color Coordinate (y value) |
|---|---|---|
| Light-emitting diode A-1 | 0.155 | 0.164 |
| Light-emitting diode A-2 | 0.156 | 0.166 |
| Light-emitting diode A-3 | 0.156 | 0.164 |
| Light-emitting diode A-4 | 0.155 | 0.164 |
| Light-emitting diode A-5 | 0.156 | 0.164 |
| Light-emitting diode A-6 | 0.155 | 0.163 |
| Light-emitting diode A-7 | 0.155 | 0.164 |
| Light-emitting diode A-8 | 0.155 | 0.166 |
| Light-emitting diode A-9 | 0.154 | 0.164 |
| Light-emitting diode A-10 | 0.156 | 0.165 |
| Light-emitting diode A-11 | 0.156 | 0.165 |
| Light-emitting diode A-12 | 0.156 | 0.166 |
| Light-emitting diode A-13 | 0.155 | 0.166 |
| Comparative diode 1 | 0.155 | 0.163 |
| Comparative diode 4 | 0.155 | 0.163 |

Referring to Table 2, it can be seen that when the color coordinates of light-emitting diodes A-1 to A-13 are compared to the color coordinates of comparative diodes 1 and 4 based on CIE 1931, light-emitting diodes A-1 to A-13 emit light having a blue color substantially the same as comparative diodes 1 and 4.

That is, it can be seen that in light-emitting diodes A-1 to A-13 according to the present invention, there is almost no variation in color coordinate while the power efficiency of the blue light-emitting diode has been enhanced, and the lifespan thereof has also been increased.

Experimental Example 3

Evaluation of Power Efficiency and Lifespan of Light-Emitting Diode

For each of light-emitting diodes B-1 to B-13 and comparative diodes 2 and 5, a sealant for UV curing was dispensed at the edge of a cover glass, to which a moisture absorbent (Getter) was attached, in a glove box under a nitrogen atmosphere, and then each of the light-emitting diodes was cohered to the cover glass, and the sealant was cured by irradiating UV light thereon. For each of light-emitting diodes B-1 to B-13 and comparative diodes 2 and 5 thus prepared above, the power efficiency was measured based on the value when the brightness was 1,000 cd/m². The unit of the result of measuring the power efficiency was lm/W. Further, the lifespan of each of light-emitting diodes B-1 to B-13 and comparative diodes 2 and 5 was measured by using a lifetime measurement device provided in a measurement oven which was maintained constantly at a temperature of 25° C. $T_{50}$ means a time for brightness of the light-emitting diode to become 50% as compared to the initial brightness, when the initial brightness of the light-emitting diode is 5,000 cd/m². The value for the lifespan may be converted into a lifespan which is expected in the case where the measurement is made under other measurement conditions based on the conversion equation publicly known to the person skilled in the art.

The measurement result is shown in Table 3.

TABLE 3

| Diode No. | Power efficiency [lm/W] | Lifespan ($T_{50}$[hr]) |
|---|---|---|
| Light-emitting diode B-1 | 6.9 | 243 |
| Light-emitting diode B-2 | 7.6 | 271 |
| Light-emitting diode B-3 | 7.3 | 256 |
| Light-emitting diode B-4 | 6.6 | 229 |
| Light-emitting diode B-5 | 6.3 | 216 |
| Light-emitting diode B-6 | 6.1 | 199 |
| Light-emitting diode B-7 | 6.2 | 205 |
| Light-emitting diode B-8 | 8.3 | 327 |
| Light-emitting diode B-9 | 7.7 | 278 |
| Light-emitting diode B-10 | 8.1 | 313 |
| Light-emitting diode B-11 | 7.7 | 275 |
| Light-emitting diode B-12 | 7.3 | 267 |
| Light-emitting diode B-13 | 8.2 | 320 |
| Comparative diode 2 | 4.9 | 152 |
| Comparative diode 5 | 5.9 | 189 |

Referring to Table 3, it can be seen that the power efficiencies of light-emitting diodes B-1 to B-13, which include the blocking layer formed of each of the compounds according to Preparation Examples 1 to 13 of the present invention, are 6.1 lm/W or more, and the average power efficiency is about 7.3 lm/W. When compared to the case where the power efficiency of comparative diode 2 is 4.9 lm/W and the power efficiency of the comparative diode 5 is 5.9 lm/W, it can be seen that the power efficiencies of light-emitting diodes B-1 to B-13 according to the present invention have been significantly increased. For example, it can be seen that the power efficiency of light-emitting diode B-8 is increased by about 40% or more compared to that of comparative diode 5.

It is shown that the lifespans of light-emitting diodes B-1 to B-13 are 199 hours or more and the average diode lifespan thereof is about 261 hours, whereas the lifespans of comparative diodes 2 and 5 are 152 hours and 189 hours, respectively. Accordingly, it can be seen that the lifespans of light-emitting diodes B-1 to B-13 according to the present invention have been significantly increased compared to the lifespans of comparative diodes 2 and 5. For example, it can be seen that the lifespan of light-emitting diode B-8 is increased by about 73% or more compared to that of comparative diode 4.

In addition, it can be seen that the bonding position of the substituent which constitutes the compound applied to the light-emitting diodes may affect physical properties of the light-emitting diodes. When physical properties of light-emitting diode B-2 and light-emitting diode B-11 are compared to each other, it is shown that the power efficiency is at the similar level. However, it can be seen that the lifespan of light-emitting diode B-11 has been enhanced by about 1.5%. As a similar case, when light-emitting diode B-3 and light-emitting diode B-12 are compared to each other, the lifespan of light-emitting diode B-12 has been enhanced by about 4.3%. Furthermore, when light-emitting diode B-10 and light-emitting diode B-13 are compared to each other, it can be seen that the lifespan of light-emitting diode B-13 has been enhanced by about 2.2%.

Experimental Example 4

Measurement of Color Coordinate of Light-Emitting Diode

For each of light-emitting diodes B-1 to B-13 and comparative diodes 2 and 5, the color coordinates were compared and measured. The color coordinate was measured based on CIE 1931. The result is shown in Table 4.

TABLE 4

| Diode No. | Color Coordinate (x value) | Color Coordinate (y value) |
| --- | --- | --- |
| Light-emitting diode B-1 | 0.155 | 0.165 |
| Light-emitting diode B-2 | 0.158 | 0.166 |
| Light-emitting diode B-3 | 0.156 | 0.166 |
| Light-emitting diode B-4 | 0.156 | 0.164 |
| Light-emitting diode B-5 | 0.154 | 0.162 |
| Light-emitting diode B-6 | 0.154 | 0.163 |
| Light-emitting diode B-7 | 0.155 | 0.164 |
| Light-emitting diode B-8 | 0.158 | 0.167 |
| Light-emitting diode B-9 | 0.154 | 0.166 |
| Light-emitting diode B-10 | 0.157 | 0.167 |
| Light-emitting diode B-11 | 0.156 | 0.165 |
| Light-emitting diode B-12 | 0.156 | 0.167 |
| Light-emitting diode B-13 | 0.157 | 0.167 |
| Comparative diode 2 | 0.155 | 0.163 |
| Comparative diode 5 | 0.155 | 0.164 |

Referring to Table 4, it can be seen that when the color coordinates of light-emitting diodes B-1 to B-13 are compared to the color coordinates of comparative diodes 2 and 5 based on CIE 1931, light-emitting diodes B-1 to B-13 emit light having a blue color substantially the same as comparative diodes 2 and 5.

That is, it can be seen that in light-emitting diodes B-1 to B-13 according to the present invention, there is almost no variation in color coordinate while the power efficiency of the blue light-emitting diode has been enhanced, and the lifespan thereof has also been increased.

Experimental Example 5

Measurement of Power Efficiency and Lifespan of Light-Emitting Diode

For each of light-emitting diodes C-1 to C-13 and comparative diodes 3 and 6, a sealant for UV curing was dispensed at the edge of a cover glass, to which a moisture absorbent (Getter) was attached, in a glove box under a nitrogen atmosphere, and then each of the light-emitting diodes was cohered to the cover glass, and the sealant was cured by irradiating UV light thereon. For each of light-emitting diodes C-1 to C-13 and comparative diodes 3 and 6 thus prepared above, the power efficiency was measured based on the value when the brightness was 1,000 cd/m². The unit of the result of measuring the power efficiency was lm/W. Further, the lifespan of each of light-emitting diodes C-1 to C-13 and comparative diodes 3 and 6 was measured by using a lifetime measurement device provided in a measurement oven which was maintained constantly at a temperature of 25° C. $T_{50}$ means a time for brightness of the light-emitting diode to become 50% as compared to the initial brightness, when the initial brightness of the light-emitting diode is 5,000 cd/m². The value for the lifespan may be converted into a lifespan which is expected in the case where the measurement is made under other measurement conditions based on the conversion equation publicly known to the person skilled in the art.

The measurement result is shown in Table 5.

TABLE 5

| Diode No. | Power efficiency [lm/W] | Lifespan ($T_{50}$[hr]) |
| --- | --- | --- |
| Light-emitting diode C-1 | 6.2 | 191 |
| Light-emitting diode C-2 | 6.6 | 187 |
| Light-emitting diode C-3 | 6.3 | 185 |
| Light-emitting diode C-4 | 5.9 | 174 |
| Light-emitting diode C-5 | 5.8 | 165 |
| Light-emitting diode C-6 | 5.6 | 167 |
| Light-emitting diode C-7 | 5.3 | 161 |
| Light-emitting diode C-8 | 7.5 | 213 |
| Light-emitting diode C-9 | 6.7 | 205 |
| Light-emitting diode C-10 | 7.4 | 210 |
| Light-emitting diode C-11 | 6.6 | 189 |
| Light-emitting diode C-12 | 6.4 | 190 |
| Light-emitting diode C-13 | 7.4 | 212 |
| Comparative diode 3 | 3.5 | 113 |
| Comparative diode 6 | 4.3 | 131 |

Referring to Table 5, it can be seen that the power efficiencies of light-emitting diodes C-1 to C-13, which include the blocking layer formed of each of the compounds according to Preparation Examples 1 to 13 of the present invention, are 5.3 lm/W or more, and the average power efficiency is about 6.4 lm/W. When compared to the case where the power efficiency of comparative diode 3 is 3.5 lm/W and the power efficiency of comparative diode 6 is 4.3 lm/W, it can be seen that the power efficiencies of light-emitting diodes C-1 to C-13 according to the present invention have been significantly increased. For example, it can be seen that the power efficiency of light-emitting diode C-8 is increased by about 74% or more compared to that of comparative diode 6.

Further, it is shown that the lifespans of light-emitting diodes C-1 to C-13 are 161 hours or more and the average diode lifespan thereof is about 188 hours, whereas the lifespans of the comparative diodes 3 and 6 are 113 hours and 131 hours, respectively. Accordingly, it can be seen that the lifespans of light-emitting diodes C-1 to C-13 according to the present invention have been significantly increased compared to the lifespans of comparative diodes 3 and 6. For example, it can be seen that the lifespan of light-emitting diode C-8 is increased by about 63% or more compared to that of comparative diode 6.

In addition, it can be seen that the bonding position of the substituent which constitutes the compound applied to the light-emitting diodes may affect physical properties of the light-emitting diodes. For example, when physical properties of light-emitting diode C-2 and light-emitting diode C-11 are compared to each other, it is shown that the power efficiency is at the equivalent level. However, it can be seen that the lifespan of light-emitting diode C-11 has been enhanced by about 1.1%. As a similar case, when light-emitting diode C-3 and light-emitting diode C-12 are compared to each other, the lifespan of light-emitting diode C-12 has been enhanced by about 2.6%. Furthermore, when light-emitting diode C-10 and light-emitting diode C-13 are compared to each other, it can be seen that the lifespan of light-emitting diode C-13 has been enhanced by about 1%.

Experimental Example 6

Measurement of Color Coordinate of Light-Emitting Diode

For each of light-emitting diodes C-1 to C-13 and comparative diodes 3 and 6, the color coordinates were compared and measured. The color coordinate was measured based on CIE 1931. The result is shown in Table 6.

TABLE 6

| Diode No. | Color Coordinate (x value) | Color Coordinate (y value) |
| --- | --- | --- |
| Light-emitting diode C-1 | 0.155 | 0.164 |
| Light-emitting diode C-2 | 0.156 | 0.165 |
| Light-emitting diode C-3 | 0.155 | 0.164 |
| Light-emitting diode C-4 | 0.154 | 0.164 |
| Light-emitting diode C-5 | 0.155 | 0.164 |
| Light-emitting diode C-6 | 0.155 | 0.163 |
| Light-emitting diode C-7 | 0.155 | 0.162 |
| Light-emitting diode C-8 | 0.156 | 0.165 |
| Light-emitting diode C-9 | 0.155 | 0.162 |
| Light-emitting diode C-10 | 0.155 | 0.165 |
| Light-emitting diode C-11 | 0.156 | 0.164 |
| Light-emitting diode C-12 | 0.156 | 0.165 |
| Light-emitting diode C-13 | 0.155 | 0.162 |
| Comparative diode 3 | 0.154 | 0.161 |
| Comparative diode 6 | 0.155 | 0.162 |

Referring to Table 6, it can be seen that when the color coordinates of light-emitting diodes C-1 to C-13 are compared to the color coordinates of comparative diodes 3 and 5 based on CIE 1931, light-emitting diodes C-1 to C-13 emit light having a blue color substantially the same as comparative diodes 3 and 6.

That is, it can be seen that in light-emitting diodes C-1 to C-13 according to the present invention, there is almost no variation in color coordinate while the power efficiency of the blue light-emitting diode has been enhanced, and the lifespan thereof has also been increased.

EXPLANATION OF CODES

| 100, 102, 104: Light-emitting diode | 10: Base substrate |
| --- | --- |
| 20: First electrode | 30, 32, 34: Hole transportable layer |
| 40: Blocking layer | 50: Light-emitting layer |
| 60: Second electrode | |

What is claimed is:
1. A light-emitting diode comprising:
a first electrode;
a second electrode;
a light-emitting layer disposed between the first electrode and the second electrode;
a hole transportable layer disposed between the first electrode and the light-emitting layer; and
a blocking layer, which is disposed between the hole transportable layer and the light-emitting layer and includes a compound represented by the following Chemical Formula 1:

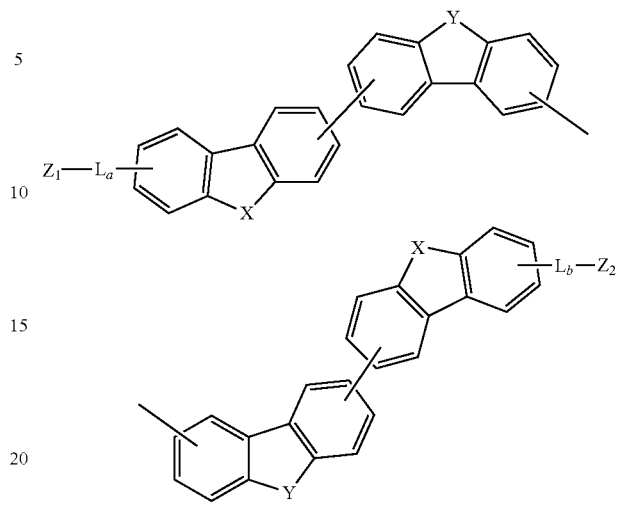

[Chemical Formula 1]

wherein
X and Y each independently represent N-$L_c$-$Ar_1$, S, O, or Si($R_1$)($R_2$),
one of X and Y is N-$L_c$-$Ar_1$, and the other is S, O, or Si($R_1$)($R_2$),
$Z_1$ and $Z_2$ each independently represent hydrogen, an alkyl group having 1 to 6 carbon atoms, an aryl group having 6 to 30 carbon atoms, or the following Chemical Formula 2 or the following Chemical Formula 3,

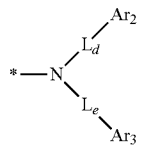

[Chemical Formula 2]

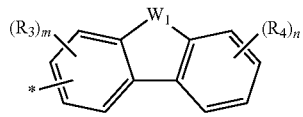

[Chemical Formula 3]

$Ar_1$, $Ar_2$, and $Ar_3$ each independently represent hydrogen, an alkyl group having 1 to 6 carbon atoms, an aryl group having 6 to 30 carbon atoms, a cycloalkyl group having 3 to 20 carbon atoms, a bicycloalkyl group having 7 to 20 carbon atoms, or the following Chemical Formula 4,

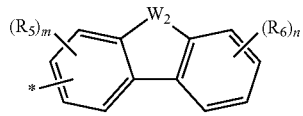

[Chemical Formula 4]

$W_1$ and $W_2$ each independently represent N-$L_f$-$Ar_4$, O, S, or Si($R_7$)($R_8$),
$R_1$, $R_2$, $R_7$, and $R_8$ each independently represent an alkyl group having 1 to 6 carbon atoms, or an aryl group having 6 to 30 carbon atoms, $R_3$, $R_4$, $R_5$, and $R_6$ each independently represent hydrogen, an alkyl group having 1 to 6 carbon atoms, or an aryl group having 6 to 30 carbon atoms, independently in each of Chemical Formulae 3 and 4, m represents an integer of 0 to 3 and n represents an integer of 0 to 4, $L_a$, $L_b$, $L_c$, $L_d$, $L_e$, and $L_f$ each independently represent *-$L_1$-$L_2$-$L_3$-$L_4$-*, $L_1$, $L_2$, $L_3$, and $L_4$ each independently represent a single bond, —O—, —S—, a linear or branched alkylene group (—(CH$_2$)$_j$—, here, j is an integer of 1 to 20) having 1 to 20 carbon atoms, an arylene group having 6 to 20 carbon atoms, a cycloalkylene group having 3 to 20 carbon atoms, or a bicycloalkylene group having 7 to 20 carbon atoms, $Ar_4$ represents hydrogen, an alkyl group having 1 to 12 carbon atoms, an aryl group having 6 to 30 carbon atoms, a cycloalkyl group having 3 to 30 carbon atoms, or a bicycloalkyl group having 7 to 30 carbon atoms, and one or more of the hydrogens of Chemical Formula 1 are each independently unsubstituted or substituted with one or more substituents selected from the group consisting of an alkyl group having 1 to 6 carbon atoms, an alkoxy group having 1 to 6 carbon atoms, an amine group unsubstituted or substituted with one or more alkyl groups having 1 to 6 carbon atoms, an aryl group having 6 to 30 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

2. The light-emitting diode of claim 1, wherein the compound of Chemical Formula 1 is represented by the following Chemical Formula 5:

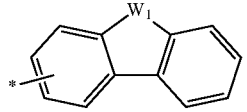

[Chemical Formula 7]

$Ar_a$, $Ar_b$, $Ar_2$, and $Ar_3$ each independently represent hydrogen, an alkyl group having 1 to 12 carbon atoms, an aryl group having 6 to 30 carbon atoms, or the following Chemical Formula 8,

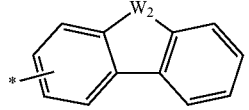

[Chemical Formula 8]

$W_1$ and $W_2$ each independently represent N—$Ar_4$, O, S, or Si($R_7$)($R_8$),

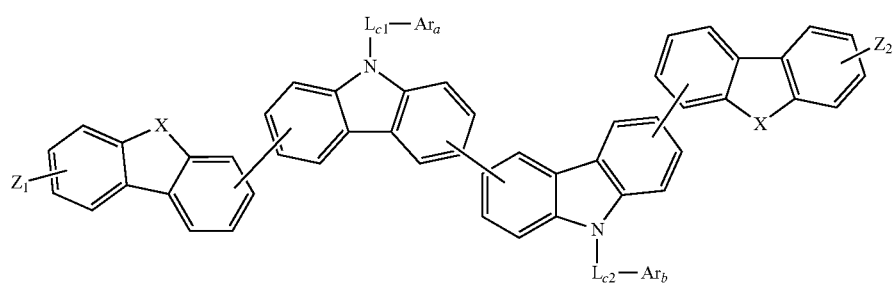

[Chemical Formula 5]

wherein

X represents S, O, or Si($R_1$)($R_2$), $L_{c1}$ and $L_{c2}$ each independently represent a single bond, —O—, —S—, an arylene group having 6 to 20 carbon atoms, or a cycloalkylene group having 3 to 20 carbon atoms, $Z_1$ and $Z_2$ each independently represent hydrogen, an alkyl group having 1 to 6 carbon atoms, an aryl group having 6 to 30 carbon atoms, or the following Chemical Formula 6 or the following Chemical Formula 7,

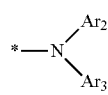

[Chemical Formula 6]

$R_1$, $R_2$, $R_7$, and $R_8$ each independently represent an alkyl group having 1 to 6 carbon atoms, or an aryl group having 6 to 30 carbon atoms, $Ar_4$ represents an alkyl group having 1 to 12 carbon atoms, or an aryl group having 6 to 30 carbon atoms, and one or more of the hydrogens of $Ar_a$, $Ar_b$, $Ar_2$, $Ar_3$, and $Ar_4$ are each independently unsubstituted or substituted with one or more substituents selected from the group consisting of an alkyl group having 1 to 6 carbon atoms, an alkoxy group having 1 to 6 carbon atoms, an amine group substituted with one or more alkyl groups having 1 to 6 carbon atoms, and an aryl group having 6 to 30 carbon atoms.

3. The light-emitting diode of claim 2, wherein the compound represented by Chemical Formula 5 is represented by the following Chemical Formula 9:

[Chemical Formula 9]

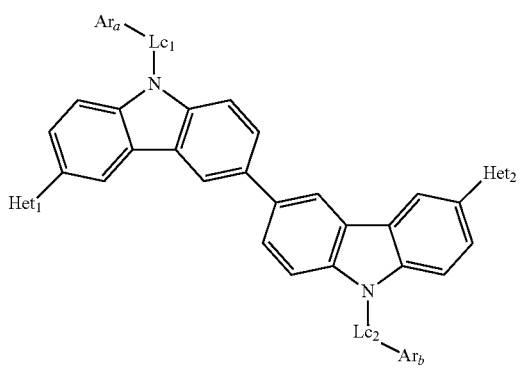

wherein $L_{c1}$ and $L_{c2}$ each independently represent a single bond, —O—, —S—, an arylene group having 6 to 20 carbon atoms, or a cycloalkylene group having 3 to 20 carbon atoms, $Ar_a$ and $Ar_b$ each independently represent hydrogen, an alkyl group having 1 to 12 carbon atoms, an aryl group having 6 to 30 carbon atoms, or the following Chemical Formula 8,

[Chemical Formula 8]

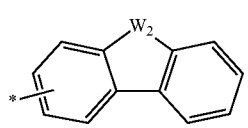

$Het_1$ and $Het_2$ each independently represent the following Chemical Formula 10 or the following Chemical Formula 11,

[Chemical Formula 10]

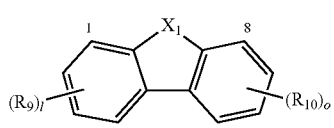

[Chemical Formula 11]

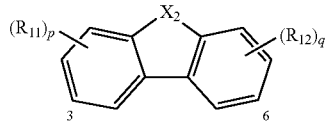

here, $W_2$ represents $N-Ar_4$, O, S, or $Si(R_7)(R_8)$, $Ar_4$ represents hydrogen, an alkyl group having 1 to 12 carbon atoms, or an aryl group having 6 to 30 carbon atoms, $X_1$ represents S or O, $X_2$ represents S, $R_7$, $R_8$, $R_9$, $R_{10}$, $R_{11}$, and $R_{12}$ each independently represent an alkyl group having 1 to 6 carbon atoms, or an aryl group having 6 to 30 carbon atoms, l, o, p, and q each independently represent an integer of 0 to 3, the substituent represented by Chemical Formula 10 is substituted with the compound of Chemical Formula 1 at the position of the 1st or 8th carbon, and the substituent represented by Chemical Formula 11 is substituted with the compound of Chemical Formula 1 at the position of the 3rd or 6th carbon.

4. The light-emitting diode of claim 2, wherein in Chemical Formula 5,

X represents S, O, or $Si(R_1)(R_2)$, $R_1$ and $R_2$ each represent a methyl group or a phenyl group, $Z_1$ and $Z_2$ are each independently represent hydrogen, a carbazolyl group, a dibenzofuranyl group, a dibenzothiophenyl group, a dibenzosilolyl group, or a diphenylamine group, and here, the carbazolyl group, the dibenzofuranyl group, the dibenzothiophenyl group, or the dibenzosilolyl group is each independently unsubstituted or substituted with one or more substituents selected from the group consisting of an alkyl group having 1 to 6 carbon atoms and an aryl group having 6 to 30 carbon atoms, and $Ar_a$ and $Ar_b$ each independently represent a phenyl group, a biphenyl group, a naphthyl group, a dibenzofuranyl group, or a dibenzothiophenyl group.

5. The light-emitting diode of claim 1, wherein the compound of Chemical Formula 1 is represented by the following Chemical Formula 12:

[Chemical Formula 12]

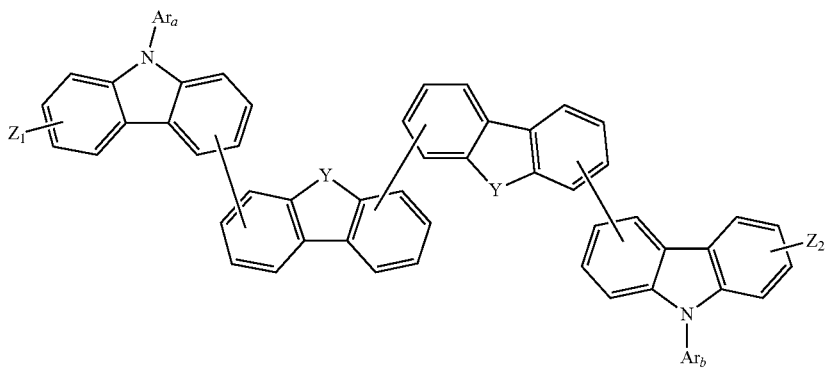

wherein
Y represents S, O, or $Si(R_1)(R_2)$,
$Z_1$ and $Z_2$ each independently represent hydrogen, the following Chemical Formula 13, or the following Chemical Formula 14,

[Chemical Formula 13]

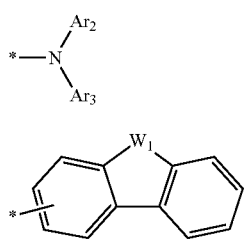

[Chemical Formula 14]

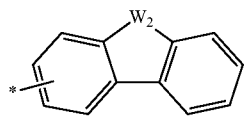

$Ar_a$, $Ar_b$, $Ar_2$, and $Ar_3$ each independently represent hydrogen, an alkyl group having 1 to 12 carbon atoms, an aryl group having 6 to 30 carbon atoms, or the following Chemical Formula 15,

[Chemical Formula 15]

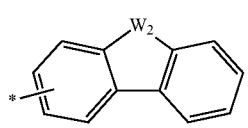

$W_1$ and $W_2$ each independently represent N—$Ar_4$, O, S, or $Si(R_7)(R_8)$,
$R_1$, $R_2$, $R_7$, and $R_8$ each independently represent an alkyl group having 1 to 6 carbon atoms, or an aryl group having 6 to 30 carbon atoms,
$Ar_4$ represents an alkyl group having 1 to 12 carbon atoms, or an aryl group having 6 to 30 carbon atoms, and
one or more of the hydrogens of $Ar_a$, $Ar_b$, $Ar_2$, $Ar_3$, and $Ar_4$ are each independently unsubstituted or substituted with one or more substituents selected from the group consisting of an alkyl group having 1 to 6 carbon atoms, an alkoxy group having 1 to 6 carbon atoms, and an amine group substituted with one or more alkyl groups having 1 to 6 carbon atoms.

6. The light-emitting diode of claim 5, wherein the compound represented by Chemical Formula 12 is represented by the following Chemical Formula 16:

[Chemical Formula 16]

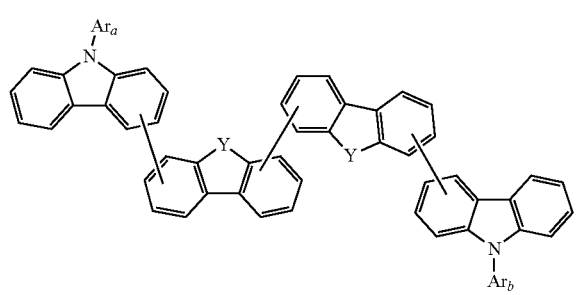

wherein
Y represents S, O, or $Si(R_1)(R_2)$,
$Ar_a$ and $Ar_b$ each independently represent an alkyl group having 1 to 6 carbon atoms, an aryl group having 6 to 30 carbon atoms, or the following Chemical Formula 17,

[Chemical Formula 17]

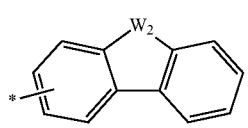

$W_2$ represents N—$Ar_4$, O, S, or $Si(R_7)(R_8)$,
$R_1$, $R_2$, $R_7$, and $R_8$ each independently represent an alkyl group having 1 to 6 carbon atoms, or an aryl group having 6 to 30 carbon atoms, and
$An_4$ represents an alkyl group having 1 to 6 carbon atoms, or an aryl group having 6 to 30 carbon atoms.

7. The light-emitting diode of claim 5, wherein in Chemical Formula 12,
Y represents S, O, or $Si(R_1)(R_2)$,
$R_1$ and $R_2$ each represent a methyl group or a phenyl group,
$Z_1$ and $Z_2$ each independently represent hydrogen, a carbazolyl group, a dibenzofuranyl group, a dibenzothiophenyl group, a dibenzosilolyl group, or a diphenylamine group, and here, the carbazolyl group, the dibenzofuranyl group, the dibenzothiophenyl group, or the dibenzosilolyl group is each independently unsubstituted or substituted with one or more substituents selected from the group consisting of an alkyl group having 1 to 6 carbon atoms and an aryl group having 6 to 30 carbon atoms, and $Ar_a$ and $Ar_b$ each independently represent a phenyl group, a biphenyl group, a naphthyl group, a dibenzofuranyl group, or a dibenzothiophenyl group.

8. The light-emitting diode of claim 1, wherein the hole transportable layer comprises a compound represented by the following Chemical Formula 18:

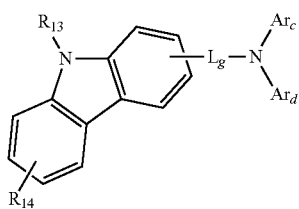

[Chemical Formula 18]

wherein
$R_{13}$ and $R_{14}$ each independently represent hydrogen, an alkyl group having 1 to 6 carbon atoms, or an aryl group having 6 to 30 carbon atoms,
$L_g$ each independently represents *-$L_5$-$L_6$-$L_7$-$L_8$-*,
$L_5$, $L_6$, $L_7$, and $L_8$ each independently represent a single bond, —O—, —S—, an arylene group having 6 to 20 carbon atoms, or a cycloalkylene group having 3 to 20 carbon atoms, and the case where $L_5$, $L_6$, $L_7$, and $L_8$ are all a single bond is excluded,
$Ar_c$ and $Ar_d$ each independently represent an aryl group having 6 to 30 carbon atoms, or the following Chemical Formula 19,

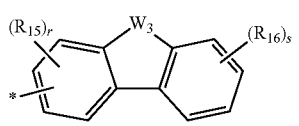

[Chemical Formula 19]

$W_3$ represents O, S, or $C(R_{17})(R_{18})$,
$R_{15}$, $R_{16}$, $R_{17}$, and $R_{18}$ each independently represent an alkyl group having 1 to 6 carbon atoms, or an aryl group having 6 to 30 carbon atoms,
r represents an integer of 0 to 3, and s represents an integer of 0 to 4.

9. The light-emitting diode of claim 8, wherein the compound represented by Chemical Formula 18 is a compound represented by the following Chemical Formula 20:

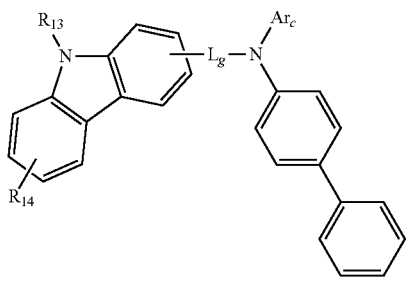

[Chemical Formula 20]

wherein
$R_{13}$ represents an aryl group having 6 to 30 carbon atoms,
$R_{14}$ represents hydrogen, $L_g$ represents an arylene group having 6 to 20 carbon atoms,
$Ar_c$ represents an aryl group having 6 to 30 carbon atoms, or the following Chemical Formula 21,

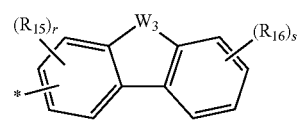

[Chemical Formula 21]

$W_3$ represents O, S, or $C(R_{17})(R_{18})$,
$R_{15}$, $R_{16}$, $R_{17}$, and $R_{18}$ each independently represent an alkyl group having 1 to 6 carbon atoms, or an aryl group having 6 to 30 carbon atoms,
r represents an integer of 0 to 2, and s represents an integer of 0 to 2.

10. The light-emitting diode of claim 9, wherein in Chemical Formula 20,
$R_{13}$ represents a phenyl group, a biphenyl group, a terphenyl group, or a naphthyl group,
$R_{14}$ represents hydrogen,
$L_g$ represents a phenylene group, a biphenylene group, a terphenylene group, or a naphthylene group, and
$Ar_c$ represents a phenyl group, a biphenyl group, a terphenyl group, a naphthyl group, dibenzothiophenyl group, a dibenzofuranyl group, a fluorenyl group, a dimethylfluorenyl group, or a diphenylfluorenyl group.

11. The light-emitting diode of claim 8, wherein the hole transportable layer comprises:
a first layer which optionally comprises a P-type dopant; and
a second layer comprising the compound of Chemical Formula 18.

12. The light-emitting diode of claim 1, wherein the light-emitting layer comprises a compound represented by the following Chemical Formula 22:

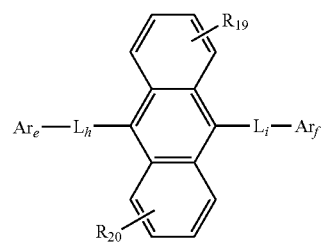

[Chemical Formula 22]

wherein
$R_{19}$ and $R_{20}$ each independently represent hydrogen, an alkyl group having 1 to 6 carbon atoms, or an aryl group having 6 to 30 carbon atoms,
$L_h$ and $L_i$ each independently represent *-$L_9$-$L_{10}$-*,
$L_9$ and $L_{10}$ each independently represent a single bond, or an arylene group having 6 to 20 carbon atoms, and
$Ar_e$ and $Ar_f$ each independently represent an aryl group having 6 to 30 carbon atoms.

13. The light-emitting diode of claim 12, wherein in Chemical Formula 22,
$R_{19}$ and $R_{20}$ each independently represent hydrogen, or an alkyl group having 1 to 6 carbon atoms,
$L_h$ and $L_i$ each independently represent *-$L_9$-$L_{10}$-*, $L_9$ and $L_{10}$ each independently represent a single bond, a phenylene group, or a naphthylene group, and $Ar_e$ and $Ar_f$ each independently represent an aryl group having 6 to 30 carbon atoms.

14. The light-emitting diode of claim 12, wherein the light-emitting layer additionally comprises a compound represented by the following Chemical Formula 23:

[Chemical Formula 23]

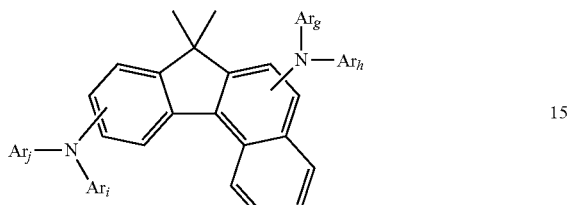

wherein $Ar_g$, $Ar_h$, $Ar_i$, and $Ar_j$ each independently represent an alkyl group having 1 to 6 carbon atoms, an aryl group having 6 to 30 carbon atoms, which is unsubstituted or substituted with a trimethylsilyl group or a cyano group.

15. An electronic apparatus comprising the light-emitting diode of claim 1.

16. The electronic apparatus of claim 15, wherein the electronic apparatus is a display device or a lighting device.

* * * * *

UNITED STATES PATENT AND TRADEMARK OFFICE
CERTIFICATE OF CORRECTION

PATENT NO. : 9,614,163 B2
APPLICATION NO. : 14/429948
DATED : April 4, 2017
INVENTOR(S) : Jeong Og Choi et al.

It is certified that error appears in the above-identified patent and that said Letters Patent is hereby corrected as shown below:

In the Claims

Column 68, Line 52, Claim 6, delete "$An_4$" and insert -- $Ar_4$ --

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*